United States Patent
Brenner

(10) Patent No.: US 6,172,214 B1
(45) Date of Patent: *Jan. 9, 2001

(54) OLIGONUCLEOTIDE TAGS FOR SORTING AND IDENTIFICATION

(75) Inventor: Sydney Brenner, Cambridge (GB)

(73) Assignee: Lynx Therapeutics, Inc., Hayward, CA (US)

( * ) Notice: Under 35 U.S.C. 154(b), the term of this patent shall be extended for 0 days.

This patent is subject to a terminal disclaimer.

(21) Appl. No.: 09/131,009

(22) Filed: Aug. 7, 1998

Related U.S. Application Data

(60) Division of application No. 08/659,453, filed on Jun. 6, 1996, now Pat. No. 5,846,719, which is a continuation-in-part of application No. 08/358,810, filed on Dec. 19, 1994, now Pat. No. 5,604,097, which is a continuation-in-part of application No. 08/322,348, filed on Oct. 13, 1994, now abandoned.

(51) Int. Cl.[7] .......................... C07H 21/04; C12N 15/11; C12N 15/00; C12Q 1/68
(52) U.S. Cl. ..................... 536/24.3; 536/23.1; 536/24.2; 536/25.4; 435/6; 435/320.1; 435/440; 435/471
(58) Field of Search ................................ 435/6, 440, 471, 435/320.1; 536/23.1, 25.4, 24.2, 24.3

(56) References Cited

U.S. PATENT DOCUMENTS

| | | | |
|---|---|---|---|
| 4,942,124 | 7/1990 | Church | 435/6 |
| 5,149,625 | 9/1992 | Church | 435/6 |
| 5,302,509 | 4/1994 | Cheeseman | 435/6 |
| 5,482,836 | 1/1996 | Cantor et al. | 435/6 |
| 5,514,543 | 5/1996 | Grossman | 435/6 |
| 5,552,278 | 9/1996 | Brenner | 435/6 |
| 5,599,675 | 2/1997 | Brenner | 435/6 |
| 5,604,097 | 2/1997 | Brenner | 435/6 |
| 5,635,400 * | 6/1997 | Brenner | 435/320.1 |
| 5,654,413 | 8/1997 | Brenner | 536/22.1 |
| 5,658,736 | 8/1997 | Wong | 435/6 |
| 5,695,934 | 12/1997 | Brenner | 435/6 |
| 5,846,719 | 12/1998 | Brenner et al. | 435/6 |
| 5,863,722 | 1/1999 | Brenner | 435/6 |

FOREIGN PATENT DOCUMENTS

| | | |
|---|---|---|
| 2036946 | 10/1991 | (CA) . |
| 303459 A3 | 2/1989 | (EP) . |
| 392546 A2 | 10/1990 | (EP) . |
| 90/03382 | 4/1990 | (WO) . |
| 92/00091 | 1/1992 | (WO) . |
| WO 92/10588 * | 6/1992 | (WO) . |
| 92/10587 | 6/1992 | (WO) . |
| 92/10588 | 6/1992 | (WO) . |
| 93/06121 | 4/1993 | (WO) . |
| 93/17126 | 9/1993 | (WO) . |
| 93/21203 | 10/1993 | (WO) . |
| 93/22680 | 11/1993 | (WO) . |
| 93/22684 | 11/1993 | (WO) . |
| 94/08051 | 4/1994 | (WO) . |
| 95/20053 | 7/1995 | (WO) . |
| 96/12014 | 4/1996 | (WO) . |
| 96/12039 | 4/1996 | (WO) . |
| 97/31256 | 8/1997 | (WO) . |

OTHER PUBLICATIONS

Brenner, S. Et Al. Proc. Natl. Acad. Sci. USA 89, 5381–5383 (Jun. 1992).*
Search Report from International Patent Application PCT/US95/12791 (published as WO 96/12014).*
Search Report from International Patent Application PCT/US96/09513 (published as WO 96/41011).*
Aslanidis, et al., "Ligation–independent Cloning of PCR Products (LIC–PCR)," *Nucleic Acids Research* 18:6069–6074 (1990).*
Beck, et al., "A Strategy for the Amplification, Purification, and Selection of M13 Templates for Large–Scale DNA Sequencing," *Analytical Biochem.* 212:498–505 (1993).*
Brenner, et al., "Encoded Combinatorial Chemistry," *Proc. Natl. Acad. Sci. U.S.A.* 89:5381–5383 (1992).*
Broude, et al., "Enhanced DNA Sequencing by Hybridization," *Proc. Natl. Acad. Sci.* 91:3072–3076 (1994).*
Brown, et al., "A New Base–Stable Linker for Solid–Phase Oligonucleotide Synthesis," *J. Chem. Soc. Commun.* 891–893 (1989).*
Chetverin, et al., "Oligonucleotide Arrays: New Concepts and Possibilities," *Biotechnology* 12:1093–1099 (1994).*
Church, et al., "Multiplex DNA Sequencing," *Science* 240:185–188 (1988).*

(List continued on next page.)

*Primary Examiner*—Robert A. Schwartzman
*Assistant Examiner*—Mark L. Shibuya
(74) *Attorney, Agent, or Firm*—Stephen C. Macevicz

(57) ABSTRACT

The invention provides a method of tracking, identifying, and/or sorting classes or subpopulations of molecules by the use of oligonucleotide tags. Oligonucleotide tags of the invention comprise oligonucleotides selected from a minimally cross-hybridizing set. Preferably, such oligonucleotides each consist of a plurality of subunits 3 to 9 nucleotides in length. A subunit of a minimally cross-hybridizing set forms a duplex or triplex having two or more mismatches with the complement of any other subunit of the same set. The number of oligonucleotide tags available in a particular embodiment depends on the number of subunits per tag and on the length of the subunit. An important aspect of the invention is the use of the oligonucleotide tags for sorting polynucleotides by specifically hybridizing tags attached to the polynucleotides to their complements on solid phase supports. This embodiment provides a readily automated system for manipulating and sorting polynucleotides, particularly useful in large-scale parallel operations, such as large-scale DNA sequencing, mRNA fingerprinting, and the like, wherein many target polynucleotides or many segments of a single target polynucleotide are sequenced simultaneously.

13 Claims, 3 Drawing Sheets

OTHER PUBLICATIONS

Coche, et al., "Reducing Bias in cDNA Sequence Representation by Molecular Selection," *Nucleic Acids Research* 22:4545–4546 (1994).*

Crick, et al., "Codes without Commas," *Proc. Natl. Acad. Sci.* 43:416–421 (1957).*

Egholm, et al., "PNA Hybridizes to Complementary Oligonucleotides Obeying the Watson–Crick Hydrogen–Bonding Rules," *Nature* 365:566–568 (1993).*

Gronostajski, "Site–Specific DNA Binding of Nuclear Factor I: Effect of the Spacer Region," *Nucleic Acids Research* 15:5545–5559 (1987).*

Gryaznov, et al., "Modulation of Oligonucleotide Duplex and Triplex Stability via Hydrophobic Interactions," *Nucleic Acids Research* 21:5909–5915 (1993).*

Hensel, et al., "Simultaneous Identification of Bacterial Virulence Genes by Negative Selection," *Science* 269:400–403 (1995).*

Hunkapiller, et al., "Large–Scale and Automated DNA Sequence Determination," *Science* 254:59–67 (1991).*

Ji and Smith, "Rapid Purification of Double–Stranded DNA by Triple–Helix–Mediated Affinity Capture," *Anal. Chem.* 65:1323–1328 (1993).*

Kuijper, et al., "Functional Cloning Vectors for Use in Directional cDNA Cloning Using Cohesive Ends Produced with T4 DNA Polymerase," *Gene* 112:147–155 (1992).*

Maskos and Southern, "Oligonucleotide Hybridization on Glass Supports: a Novel Linker for Oligonucleotide Synthesis and Hybridization Properties of Oligonucleotides Synthesized in situ," *Nucleic Acids Research* 20:1679–1684 (1992).*

Matteucci, et al., "Targeted Random Mutagenesis: the Use of Ambiguously Synthesized Oligonucleotides to Mutagenize Sequences Immediately 5' of an ATG Initiation Codon," *Nucleic Acids Research* 11:3113–3121 (1983).*

Matthews and Kricka, "Analytical Strategies for the Use of DNA Probes," *Anal. Biochem.* 169:1–25 (1988).*

Needels, et al., "Generation and Screening of an Oligonucleotide–Encoded Synthetic Peptide Library," *Proc. Natl. Acad. Sci.* 90:10700–10704 (1993).*

Nielsen, et al., "Synthesis Methods for the Implementation of Encoded Combinatorial Chemistry," *J. Am. Chem. Soc.* 115:9812–9813 (1993).*

Ohlmeyer, et al., "Complex Synthetic Chemical Libraries Indexed with Molecular Tags," *Proc. Natl. Acad. Sci.* 90:10922–10926 (1993).*

Oliphant, et al., "Cloning of Random–Sequence Oligodeoxynucleotides," *Gene* 44:177–183 (1986).*

Oliphant and Struhl, "Defining the Consensus Sequences of *E. Coli* Promoter Elements by Random Selection," *Nucleic Acids Research* 16:7673–7683 (1988).*

Rychlik, W., and Rhoads, R.E., "A Computer Program for Choosing Optimal Oligonucleotides for Filter Hybridization, Sequencing, and in vitro Amplification of DNA," *Nucleic Acids Research* 17(21):8543–8551 (1989).*

Shoemaker, et al., "Quantitative Phenotypic Analysis of Yeast Deletion Mutants Using a Highly Parallel Molecular Bar–Coding Strategy," *Nature Genetics* 14:450–456 (1996).*

Wetmur, "DNA Probes: Applications of the Principles of Nucleic Acid Hybridization," *Critical Reviews in Biochemistry and Molecular Biology* 26:227–259 (1991).*

Yang and Youvan, "A Prospectus for Multispectral–Multiplex DNA Sequencing," *Biotechnology* 7:576–580 (1989).*

* cited by examiner

OLIGONUCLEOTIDE TAGS FOR SORTING AND IDENTIFICATION

This is a divisional of Ser. No. 08/659,453 filed Jun. 6, 1996 now U.S. Pat. No. 5,896,719, which is a continuation-in-part of Ser. No. 08/358,810 filed Dec. 19, 1994, now U.S. Pat. No. 5,604,097, which is a continuation-in-part of Ser. No. 08/322,348 filed Oct. 13, 1994, now abandoned, all of which are incorporated herein by reference.

FIELD OF THE INVENTION

The invention relates generally to methods for identifying, sorting, and/or tracking molecules, especially polynucleotides, with oligonucleotide tags, and more particularly, to a method of sorting and analyzing such tagged polynucleotides by specific hybridization of the tags to their complements.

BACKGROUND

Specific hybridization of oligonucleotides and their analogs is a fundamental process that is employed in a wide variety of research, medical, and industrial applications, including the identification of disease-related polynucleotides in diagnostic assays, screening for clones of novel target polynucleotides, identification of specific polynucleotides in blots of mixtures of polynucleotides, amplification of specific target polynucleotides, therapeutic blocking of inappropriately expressed genes, DNA sequencing, and the like, e.g. Sambrook et al, Molecular Cloning: A Laboratory Manual, 2nd Edition (Cold Spring Harbor Laboratory, New York, 1989); Keller and Manak, DNA Probes, 2nd Edition (Stockton Press, New York, 1993); Milligan et al, J. Med. Chem., 36: 1923–1937 (1993); Drznanac et al, Science, 260: 1649–1652 (1993); Bains, J. DNA Sequencing and Mapping, 4: 143–150 (1993).

Specific hybridization has also been proposed as a method of tracking, retrieving, and identifying compounds labeled with oligonucleotide tags. For example, in multiplex DNA sequencing oligonucleotide tags are used to identify electrophoretically separated bands on a gel that consist of DNA fragments generated in the same sequencing reaction. In this way, DNA fragments from many sequencing reactions are separated on the same lane of a gel which is then blotted with separate solid phase materials on which the fragment bands from the separate sequencing reactions are visualized with oligonucleotide probes that specifically hybridize to complementary tags, Church et al, Science, 240: 185–188 (1988). Similar uses of oligonucleotide tags have also been proposed for identifying explosives, potential pollutants, such as crude oil, and currency for prevention and detection of counterfeiting, e.g. reviewed by Dollinger, pages 265–274 in Mullis et al, editors, The Polymerase Chain Reaction (Birkhauser, Boston, 1994). More recently, systems employing oligonucleotide tags have also been proposed as a means of manipulating and identifying individual molecules in complex combinatorial chemical libraries, for example, as an aid to screening such libraries for drug candidates, Brenner and Lerner, Proc. Natl. Acad. Sci., 89: 5381–5383 (1992); Alper, Science, 264: 1399–1401 (1994); and Needels et al, Proc. Natl. Acad. Sci., 90: 10700–10704 (1993).

The successful implementation of such tagging schemes depends in large part on the success in achieving specific hybridization between a tag and its complementary probe. That is, for an oligonucleotide tag to successfully identify a substance, the number of false positive and false negative signals must be minimized. Unfortunately, such spurious signals are not uncommon because base pairing and base stacking free energies vary widely among nucleotides in a duplex or triplex structure. For example, a duplex consisting of a repeated sequence of deoxyadenosine (A) and thymidine (T) bound to its complement may have less stability than an equal-length duplex consisting of a repeated sequence of deoxyguanosine (G) and deoxycytidine (C) bound to a partially complementary target containing a mismatch. Thus, if a desired compound from a large combinatorial chemical library were tagged with the former oligonucleotide, a significant possibility would exist that, under hybridization conditions designed to detect perfectly matched AT-rich duplexes, undesired compounds labeled with the GC-rich oligonucleotide—even in a mismatched duplex—would be detected along with the perfectly matched duplexes consisting of the AT-rich tag. In the molecular tagging system proposed by Brenner et al (cited above), the related problem of mis-hybridizations of closely related tags was addressed by employing a so-called "comma-less" code, which ensures that a probe out of register (or frame shifted) with respect to its complementary tag would result in a duplex with one or more mismatches for each of its five or more three-base words, or "codons."

Even though reagents, such as tetramethylammonium chloride, are available to negate base-specific stability differences of oligonucleotide duplexes, the effect of such reagents is often limited and their presence can be incompatible with, or render more difficult, further manipulations of the selected compounds, e.g. amplification by polymerase chain reaction (PCR), or the like.

Such problems have made the simultaneous use of multiple hybridization probes in the analysis of multiple or complex genetic loci, e.g. via multiplex PCR, reverse dot blotting, or the like, very difficult. As a result, direct sequencing of certain loci, e.g. HLA genes, has been promoted as a reliable alternative to indirect methods employing specific hybridization for the identification of genotypes, e.g. Gyllensten et al, Proc. Natl. Acad. Sci., 85: 7652–7656 (1988).

The ability to sort cloned and identically tagged DNA fragments onto distinct solid phase supports would facilitate such sequencing, particularly when coupled with a non gel-based sequencing methodology simultaneously applicable to many samples in parallel.

In view of the above, it would be useful if there were available an oligonucleotide-based tagging system which provided a large repertoire of tags, but which also minimized the occurrence of false positive and false negative signals without the need to employ special reagents for altering natural base pairing and base stacking free energy differences. Such a tagging system would find applications in many areas, including construction and use of combinatorial chemical libraries, large-scale mapping and sequencing of DNA, genetic identification, medical diagnostics, and the like.

SUMMARY OF THE INVENTION

An object of my invention is to provide a molecular tagging system for tracking, retrieving, and identifying compounds.

Another object of my invention is to provide a method for sorting identical molecules, or subclasses of molecules, especially polynucleotides, onto surfaces of solid phase materials by the specific hybridization of oligonucleotide tags and their complements.

A further object of my invention is to provide a method for analyzing gene expression patterns in diseased and normal tissues.

A still further object of my invention is to provide a system for tagging and sorting many thousands of fragments, especially randomly overlapping fragments, of a target polynucleotide for simultaneous analysis and/or sequencing.

Another object of my invention is to provide a rapid and reliable method for sequencing target polynucleotides having a length in the range of a few hundred basepairs to several tens of thousands of basepairs.

A further object of my invention is to provide a method for reducing the number of separate template preparation steps required in large scale sequencing projects employing conventional Sanger-based sequencing techniques.

My invention achieves these and other objects by providing a method and materials for tracking, identifying, and/or sorting classes or subpopulations of molecules by the use of oligonucleotide tags. An important feature of the invention is that the oligonucleotide tags are members of a minimally cross-hybridizing set of oligonucleotides. The sequences of oligonucleotides of such a set differ from the sequences of every other member of the same set by at least two nucleotides. Thus, each member of such a set cannot form a duplex (or triplex) with the complement of any other member with less than two mismatches. Complements of oligonucleotide tags of the invention, referred to herein as "tag complements," may comprise natural nucleotides or non-natural nucleotide analogs. Preferably, tag complements are attached to solid phase supports. Such oligonucleotide tags when used with their corresponding tag complements provide a means of enhancing specificity of hybridization for sorting, tracking, or labeling molecules, especially polynucleotides.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides, such set having a maximum size of 332 (when composed of 3 kinds of nucleotides and counted using a computer program such as disclosed in Appendix Ic). Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$ or 729, 12-mers. The number 9 is number of oligonucleotides listed by the computer program of Appendix Ia, which assumes, as with the 10-mers, that only 3 of the 4 different types of nucleotides are used. The set is described as "maximal" because the computer programs of Appendices Ia-c provide the largest set for a given input (e.g. length, composition, difference in number of nucleotides between members). Additional minimally cross-hybridizing sets may be formed from subsets of such calculated sets.

Oligonucleotide tags may be single stranded and be designed for specific hybridization to single stranded tag complements by duplex formation or for specific hybridization to double stranded tag complements by triplex formation. Oligonucleotide tags may also be double stranded and be designed for specific hybridization to single stranded tag complements by triplex formation.

When synthesized combinatorially, an oligonucleotide tag of the invention preferably consists of a plurality of subunits, each subunit consisting of an oligonucleotide of 3 to 9 nucleotides in length wherein each subunit is selected from the same minimally cross-hybridizing set. In such embodiments, the number of oligonucleotide tags available depends on the number of subunits per tag and on the length of the subunits. The number is generally much less than the number of all possible sequences the length of the tag, which for a tag n nucleotides long would be $4^n$.

In one aspect of my invention, complements of oligonucleotide tags attached to a solid phase support are used to sort polynucleotides from a mixture of polynucleotides each containing a tag. In this embodiment, complements of the oligonucleotide tags are synthesized on the surface of a solid phase support, such as a microscopic bead or a specific location on an array of synthesis locations on a single support, such that populations of identical sequences are produced in specific regions. That is, the surface of each support, in the case of a bead, or of each region, in the case of an array, is derivatized by only one type of complement which has a particular sequence. The population of such beads or regions contains a repertoire of complements with distinct sequences. As used herein in reference to oligonucleotide tags and tag complements, the term "repertoire" means the set of minimally cross-hybridizing set of oligonucleotides that make up the tags in a particular embodiment or the corresponding set of tag complements.

The polynucleotides to be sorted each have an oligonucleotide tag attached, such that different polynucleotides have different tags. As explained more fully below, this condition is achieved by employing a repertoire of tags substantially greater than the population of polynucleotides and by taking a sufficiently small sample of tagged polynucleotides from the full ensemble of tagged polynucleotides After such sampling, when the populations of supports and polynucleotides are mixed under conditions which permit specific hybridization of the oligonucleotide tags with their respective complements, identical polynucleotides sort onto particular beads or regions. The sorted populations of polynucleotides can then be manipulated on the solid phase support by micro-biochemical techniques.

Generally, the method of my invention comprises the following steps: (a) attaching an oligonucleotide tag from a repertoire of tags to each molecule in a population of molecules (i) such that substantially all different molecules or different subpopulations of molecules in the population have different oligonucleotide tags attached and (ii) such that each oligonucleotide tag from the repertoire is selected from the same minimally cross-hybridizing set; and (b) sorting the molecules of the population onto one or more solid phase supports by specifically hybridizing the oligonucleotide tags with their respective complements attached to such supports.

An important aspect of my invention is the use of the oligonucleotide tags to sort polynucleotides for parallel sequence determination. Preferably, such sequencing is carried out by the following steps: (a) generating from the target polynucleotide a plurality of fragments that cover the target polynucleotide; (b) attaching an oligonucleotide tag from a repertoire of tags to each fragment of the plurality (i) such substantially all different fragments have different oligonucleotide tags attached and (ii) such that each oligonucleotide tag from the repertoire is selected from the same minimally cross-hybridizing set; (c) sorting the fragments onto one or more solid phase supports by specifically hybridizing the oligonucleotide tags with their respective complements attached to the solid phase supports; (d) determining the nucleotide sequence of a portion of each of the fragments of the plurality, preferably by a single-base sequencing methodology as described below; and (e) determining the nucleotide sequence of the target polynucleotide by collating the sequences of the fragments.

Another important aspect of my invention is the determination of a profile, or a frequency distribution, of genes being expressed in a given tissue or cell type, wherein each such gene is identified by a portion of its sequence. Preferably, such frequency distribution is determined by the following steps: (a) forming a cDNA library from a population of mRNA molecules, each cDNA molecule in the cDNA library having an oligonucleotide tag attached, (i) such that substantially all different cDNA molecules have different oligonucleotide tags attached and (ii) such that each oligonucleotide tag from the repertoire is selected from the same minimally cross-hybridizing set; (b) sorting the cDNA molecules by specifically hybridizing the oligonucleotide tags with their respective complements attached to one or more solid phase supports; (c) determining the nucleotide sequence of a portion of each of the sorted cDNA molecules; and (d) forming a frequency distribution of mRNA molecules from the nucleotide sequences of the portions of sorted cDNA molecules.

My invention overcomes a key deficiency of current methods of tagging or labeling molecules with oligonucleotides: By coding the sequences of the tags in accordance with the invention, the stability of any mismatched duplex or triplex between a tag and a complement to another tag is far lower than that of any perfectly matched duplex between the tag and its own complement. Thus, the problem of incorrect sorting because of mismatch duplexes of GC-rich tags being more stable than perfectly matched AT-rich tags is eliminated. When used in combination with solid phase supports, such as microscopic beads, my invention provides a readily automated system for manipulating and sorting polynucleotides, particularly useful in large-scale parallel operations, such as large-scale DNA sequencing, wherein many target polynucleotides or many segments of a single target polynucleotide are sequenced and/or analyzed simultaneously.

DEFINITIONS

Figure 1:
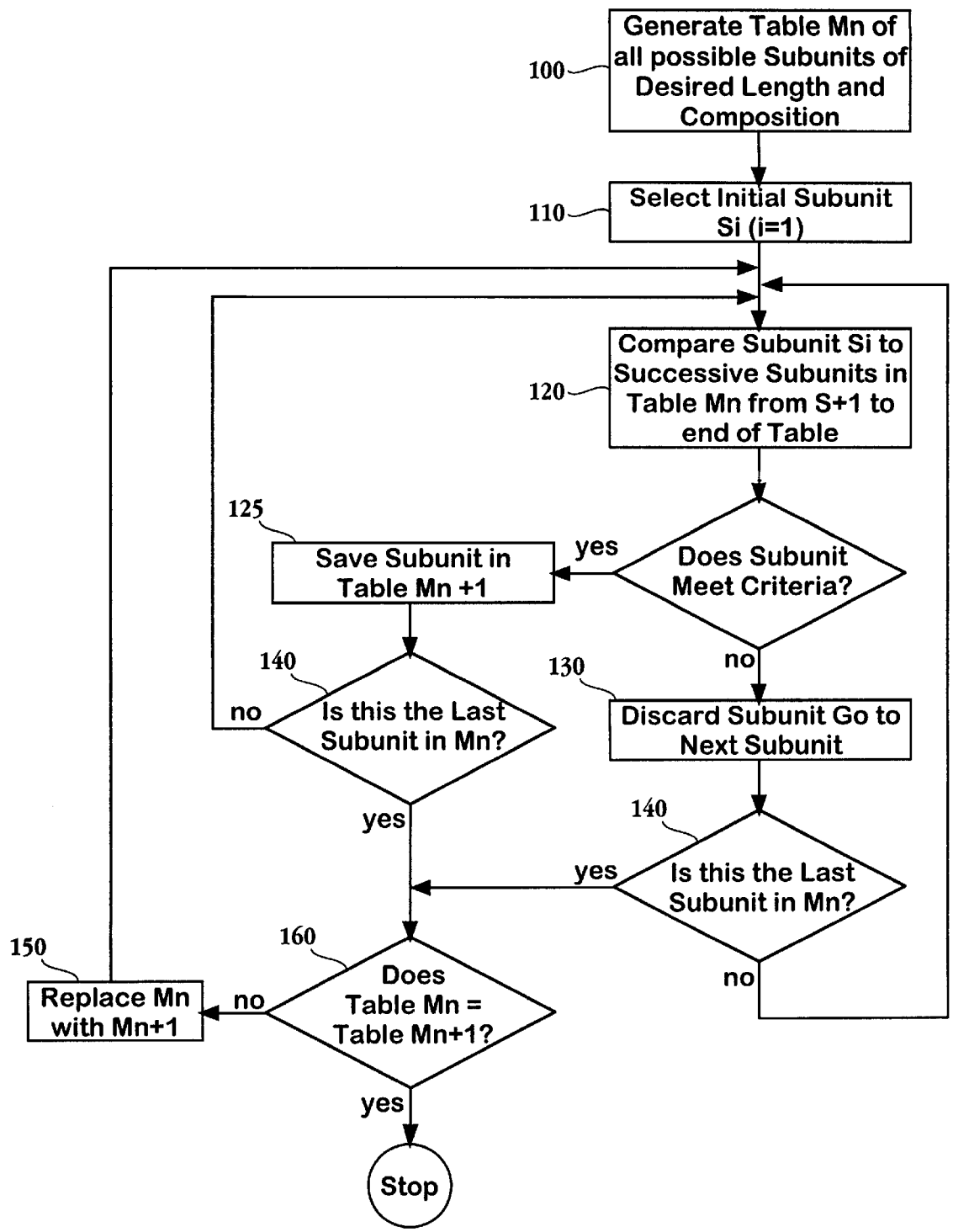
FIG. 1 is a flow chart illustrating a general algorithm for generating minimally cross-hybridizing sets.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)(not C)C-(not C)-C . . . " and the like.

As used herein, the term "complexity" in reference to a population of polynucleotides means the number of different species of molecule present in the population.

DETAILED DESCRIPTION OF THE INVENTION

The invention provides a method of labeling and sorting molecules, particularly polynucleotides, by the use of oligonucleotide tags. The oligonucleotide tags of the invention belong to minimally cross-hybridizing sets of oligonucleotides. Thus, the sequences of any two oligonucleotide tags of a repertoire will never be "closer" than differing by two nucleotides. In particular embodiments, sequences of any two oligonucleotide tags of a repertoire can be even "fiurther" apart, e.g. by designing a minimally cross-hybridizing set such that oligonucleotides cannot form a duplex or triplex with the complement of another member of the same set with less than three mismatched nucleotides, and so on. In such embodiments, greater specificity is achieved, but the total repertoire of tags is smaller. Thus, for tags of a given length, a trade off must be made between the degree of specificity desired and the size of repertoire desired. The invention is particularly useful in labeling and sorting polynucleotides for parallel operations, such as sequencing, fingerprinting or other types of analysis.

Oligonucleotide Tars and Tag Complements

The nucleotide sequences of oligonucleotides of a minimally cross-hybridizing set are conveniently enumerated by simple computer programs following the general algorithm illustrated in FIG. 1, and as exemplified by programs whose source codes are listed in Appendices Ia and Ib. Program minhx of Appendix Ia computes all minimally crosshybridizing sets having 4-mer subunits composed of three kinds of nucleotides. Program tagN of Appendix Ib enumerates longer oligonucleotides of a minimally crosshybridizing set. Similar algorithms and computer programs are readily written for listing oligonucleotides of minimally cross-hybridizing sets for any embodiment of the invention. Table I below provides guidance as to the size of sets of minimally cross-hybridizing oligonucleotides for the indicated lengths and number of nucleotide differences. The above computer programs were used to generate the numbers.

TABLE I

| Oligo-nucleotide Word Length | Nucleotide Difference between Oligo-nucleotides of Minimally Cross-Hybridizing Set | Maximal Size of Minimally Cross-Hybridizing Set | Size of Repertoire with Four Words | Size of Repertoire with Five Words |
| --- | --- | --- | --- | --- |
| 4 | 3 | 9 | 6561 | $5.90 \times 10^4$ |
| 6 | 3 | 27 | $5.3 \times 10^5$ | $1.43 \times 10^7$ |

TABLE I-continued

| Oligo-nucleotide Word Length | Nucleotide Difference between Oligo-nucleotides of Minimally Cross-Hybridizing Set | Maximal Size of Minimally Cross-Hybridizing Set | Size of Repertoire with Four Words | Size of Repertoire with Five Words |
| --- | --- | --- | --- | --- |
| 7 | 4 | 27 | $5.3 \times 10^5$ | $1.43 \times 10^7$ |
| 7 | 5 | 8 | 4096 | $3.28 \times 10^4$ |
| 8 | 3 | 190 | $1.30 \times 10^9$ | $2.48 \times 10^{11}$ |
| 8 | 4 | 62 | $1.48 \times 10^7$ | $9.16 \times 10^8$ |
| 8 | 5 | 18 | $1.05 \times 10^5$ | $1.89 \times 10^6$ |
| 9 | 5 | 39 | $2.31 \times 10^6$ | $9.02 \times 10^7$ |
| 10 | 5 | 332 | $1.21 \times 10^{10}$ | |
| 10 | 6 | 28 | $6.15 \times 10^5$ | $1.72 \times 10^7$ |
| 11 | 5 | 187 | | |
| 18 | 6 | ≈25000 | | |
| 18 | 12 | 24 | | |

For some embodiments of the invention, where extremely large repertoires of tags are not required, oligonucleotide tags of a minimally cross-hybridizing set may be separately synthesized. Sets containing several hundred to several thousands, or even several tens of thousands, of oligonucleotides may be synthesized directly by a variety of parallel synthesis approaches, e.g. as disclosed in Frank et al, U.S. Pat. No. 4,689,405; Frank et al, Nucleic Acids Research, 11: 4365–4377 (1983); Matson et al, Anal. Biochem., 224: 110–116 (1995); Fodor et al, International application PCT/US93/04145; Pease et al, Proc. Natl. Acad. Sci., 91: 5022–5026 (1994); Southern et al, J. Biotechnology, 35: 217–227 (1994), Brennan, International application PCT/US94/05896; Lashkari et al, Proc. Natl. Acad. Sci., 92: 7912–7915 (1995); or the like.

Preferably, oligonucleotide tags of the invention are synthesized combinatorially out of subunits between three and six nucleotides in length and selected from the same minimally cross-hybridizing set. For oligonucletides in this range, the members of such sets may be enumerated by computer programs based on the algorithm of FIG. 1.

Figure 3:
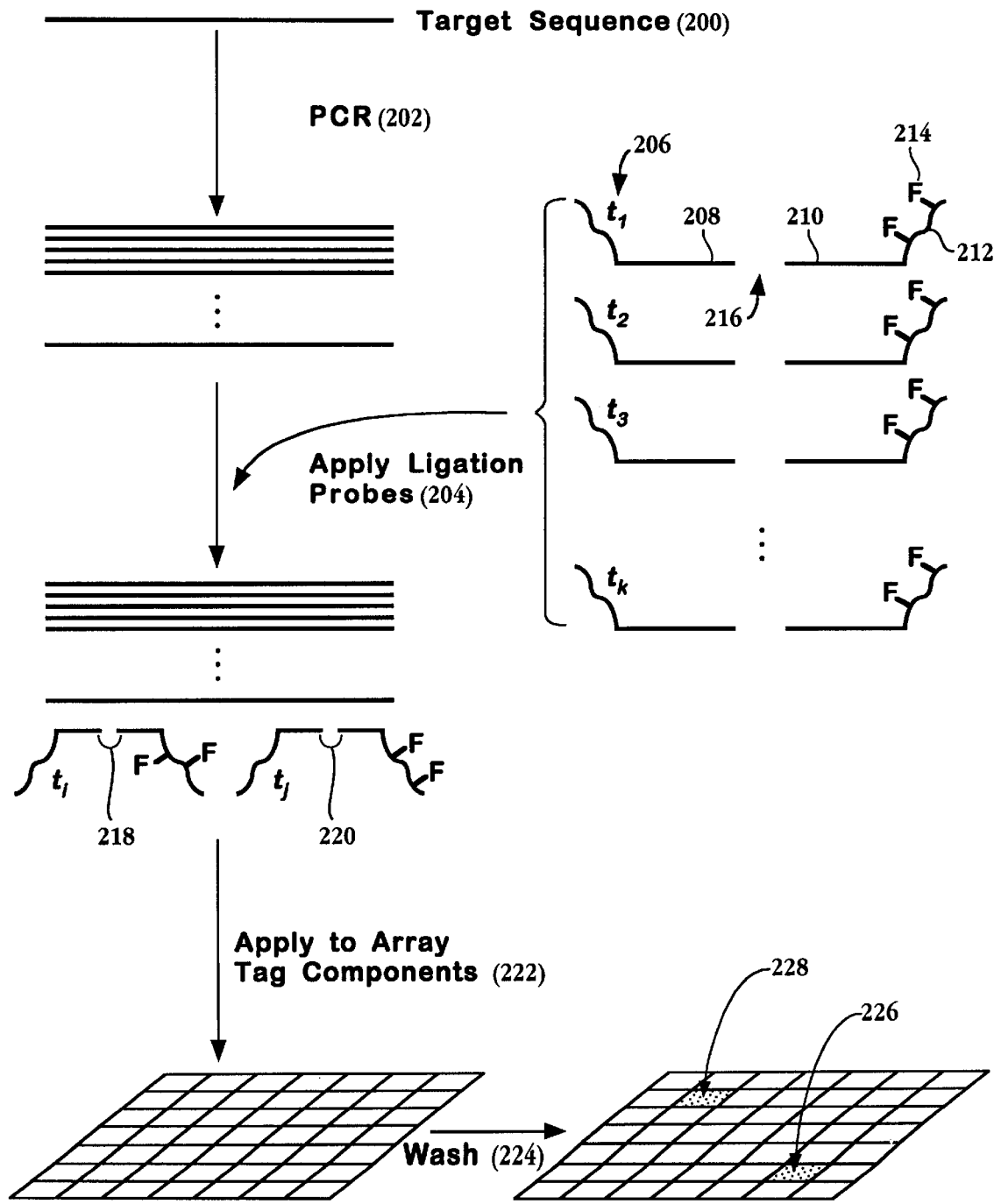
FIG. 3 illustrates an embodiment for genotyping by sorting ligated probes onto a solid phase support.

The algorithm of FIG. 3 is implemented by first defining the characteristics of the subunits of the minimally crosshybridizing set, i.e. length, number of base differences between members, and composition, e.g. do they consist of two, three, or four kinds of bases. A table $M_n$, n=1, is generated (100) that consists of all possible sequences of a given length and composition. An initial subunit $S_1$ is selected and compared (120) with successive subunits $S_i$ for i=n+1 to the end of the table. Whenever a successive subunit has the required number of mismatches to be a member of the minimally cross-hybridizing set, it is saved in a new table $M_{n+1}$ (125), that also contains subunits previously selected in prior passes through step 120. For example, in the first set of comparisons, $M_2$ will contain $S_1$; in the second set of comparisons, $M_3$ will contain $S_1$ and $S_2$; in the third set of comparisons, $M_4$ will contain $S_1$, $S_2$, and $S_3$; and so on. Similarly, comparisons in table $M_j$ will be between $S_j$ and all successive subunits in $M_j$. Note that each successive table $M_{n+1}$ is smaller than its predecessors as subunits are eliminated in successive passes through step 130. After every subunit of table $M_n$ has been compared (140) the old table is replaced by the new table $M_{n+1}$, and the next round of comparisons are begun. The process stops (160) when a table $M_n$ is reached that contains no successive subunits to compare to the selected subunit $S_i$, i.e. $M_n = M_{n+1}$.

Preferably, minimally cross-hybridizing sets comprise subunits that make approximately equivalent contributions to duplex stability as every other subunit in the set. In this way, the stability of perfectly matched duplexes between every subunit and its complement is approximately equal. Guidance for selecting such sets is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83: 3746–3750 (1986); Wetmur, Crit. Rev. Biochem. Mol. Biol., 26: 227–259 (1991);and the like. For shorter tags, e.g. about 30 nucleotides or less, the algorithm described by Rychlik and Wetmur is preferred, and for longer tags, e.g. about 30–35 nucleotides or greater, an algorithm disclosed by Suggs et al, pages 683–693 in Brown, editor, ICN-UCLA Symp. Dev. Biol., Vol. 23 (Academic Press, New York, 1981) may be conveniently employed. Clearly, the are many approaches available to one skilled in the art for designing sets of minimally cross-hybridizing subunits within the scope of the invention. For example, to minimize the affects of different base-stacking energies of terminal nucleotides when subunits are assembled, subunits may be provided that have the same terminal nucleotides. In this way, when subunits are linked, the sum of the base-stacking energies of all the adjoining terminal nucleotides will be the same, thereby reducing or eliminating variability in tag melting temperatures.

A "word" of terminal nucleotides, shown in italic below, may also be added to each end of a tag so that a perfect match is always formed between it and a similar terminal "word" on any other tag complement. Such an augmented tag would have the form:

| w | $w_1$ | $w_2 \ldots w_{k-1}$ | $w_k$ | w |
|---|---|---|---|---|
| w' | $w_1'$ | $w_2' \ldots w_{k-1}'$ | $w_k'$ | w' | where the primed W's indicate complements. With ends of tags always forming perfectly matched duplexes, all mismatched words will be internal mismatches thereby reducing the stability of tag-complement duplexes that otherwise would have mismatched words at their ends. It is well known that duplexes with internal mismatches are significantly less stable than duplexes with the same mismatch at a terminus.

A preferred embodiment of minimally cross-hybridizing sets are those whose subunits are made up of three of the four natural nucleotides. As will be discussed more fully below, the absence of one type of nucleotide in the oligonucleotide tags permits target polynucleotides to be loaded onto solid phase supports by use of the 3'→5' exonuclease activity of a DNA polymerase. The following is an exemplary minimally cross-hybridizing set of subunits each comprising four nucleotides selected from the group consisting of A, G, and T:

TABLE II

| Word: | $w_1$ | $w_2$ | $w_3$ | $w_4$ |
|---|---|---|---|---|
| Sequence: | GATT | TGAT | TAGA | TTTG |
| Word: | $w_5$ | $w_6$ | $w_7$ | $w_8$ |
| Sequence: | GTAA | AGTA | ATGT | AAAG |

In this set, each member would form a duplex having three mismatched bases with the complement of every other member.

Further exemplary minimally cross-hybridizing sets are listed below in Table III. Clearly, additional sets can be generated by substituting different groups of nucleotides, or by using subsets of known minimally cross-hybridizing sets.

Table III

Exemplary Minimally Cross-Hybridizing Sets of 4-mer Subunits

| Set 1 | Set 2 | Set 3 | Set 4 | Set 5 | Set 6 |
|---|---|---|---|---|---|
| CATT | ACCC | AAAC | AAAG | AACA | AACG |
| CTAA | AGGG | ACCA | ACCA | ACAC | ACAA |
| TCAT | CACG | AGGG | AGGC | AGGG | AGGC |
| ACTA | CCGA | CACG | CACC | CAAG | CAAC |
| TACA | CGAC | CCGC | CCGG | CCGC | CCGG |
| TTTC | GAGC | CGAA | CGAA | CGCA | CGCA |
| ATCT | GCAG | GAGA | GAGA | GAGA | GAGA |
| AAAC | GGCA | GCAG | GCAC | GCCG | GCCC |
|  | AAAA | GGCC | GGCG | GGAC | GGAG |

| Set 7 | Set 8 | Set 9 | Set 10 | Set 11 | Set 12 |
|---|---|---|---|---|---|
| AAGA | AAGC | AAGG | ACAG | ACCG | ACGA |
| ACAC | ACAA | ACAA | AACA | AAAA | AAAC |
| AGCG | AGCG | AGCC | AGGC | AGGC | AGCG |
| CAAG | CAAG | CAAC | CAAC | CACC | CACA |
| CCCA | CCCC | CCCG | CCGA | CCGA | CCAG |
| CGGC | CGGA | CGGA | CGCG | CGAG | CGGC |
| GACC | GACA | GACA | GAGG | GAGG | GAGG |
| GCGG | GCGG | GCGC | GCCC | GCAC | GCCC |
| GGAA | GGAC | GGAG | GGAA | GGCA | GGAA |

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are capable of specific hybridization. In some embodiments, tags may comprise naturally occurring nucleotides that permit processing or manipulation by enzymes, while the corresponding tag complements may comprise non-natural nucleotide analogs, such as peptide nucleic acids, or like compounds, that promote the formation of more stable duplexes during sorting.

When microparticles are used as supports, repertoires of oligonucleotide tags and tag complements may be generated by subunit-wise synthesis via "split and mix" techniques, e.g. as disclosed in Shortle et al, International patent application PCT/US93/03418 or Lyttle et al, Biotechniques, 19: 274–280 (1995). Briefly, the basic unit of the synthesis is a subunit of the oligonucleotide tag. Preferably, phosphoramidite chemistry is used and 3' phosphoramidite oligonucleotides are prepared for each subunit in a minimally cross-hybridizing set, e.g. for the set first listed above, there would be eight 4-mer 3'-phosphoramidites. Synthesis proceeds as disclosed by Shortle et al or in direct analogy with the techniques employed to generate diverse oligonucleotide libraries using nucleosidic monomers, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; Lam et al, Nature, 354: 82–84 (1991); Zuckerman et al, Int. J. Pept. Protein Research, 40: 498–507 (1992); and the like. Generally, these techniques simply call for the application of mixtures of the activated monomers to the growing oligonucleotide during the coupling steps. Preferably, oligonucleotide tags and tag complements are synthesized on a DNA synthesizer having a number of synthesis chambers which is greater than or equal to the number of different kinds of words used in the construction of the tags. That is, preferably 'there is a synthesis chamber corresponding to each type of word. In this embodiment, words are added nucleotide-by-nucleotide, such that if a word consists of five nucleotides there are five monomer couplings in each synthesis chamber. After a word is completely synthesized, the synthesis supports are removed from the chambers, mixed, and redistributed back to the chambers for the next cycle of word addition. This latter embodiment takes advantage of the high coupling yields of monomer addition, e.g. in phosphoramidite chemistries.

Double stranded forms of tags may be made by separately synthesizing the complementary strands followed by mixing under conditions that permit duplex formation. Alternatively, double stranded tags may be formed by first synthesizing a single stranded repertoire linked to a known oligonucleotide sequence that serves as a primer binding site. The second strand is then synthesized by combining the single stranded repertoire with a primer and extending with a polymerase. This latter approach is described in Oliphant et al, Gene, 44: 177–183 (1986). Such duplex tags may then be inserted into cloning vectors along with target polynucleotides for sorting and manipulating the target polynucleotide in accordance with the invention.

When tag complements are employed that are made up of nucleotides that have enhanced binding characteristics, such as PNAs or oligonucleotide N3'→P5' phosphoramidates, sorting can be implemented through the formation of D-loops between tags comprising natural nucleotides and their PNA or phosphoramidate complements, as an alternative to the "stripping" reaction employing the 3'→5' exonuclease activity of a DNA polymerase to render a tag single stranded.

Oligonucleotide tags of the invention may range in length from 12 to 60 12 to 30, or 15 to 24 nucleotides or basepairs. Preferably, oligonucleotide tags range in length from 18 to 40 nucleotides or basepairs. More preferably, oligonucleotide tags range in length from 25 to 40 nucleotides or basepairs. In terms of preferred and more preferred numbers of subunits, these ranges may be expressed as follows:

TABLE IV

Numbers of Subunits in Tags in Preferred Embodiments

| Monomers in Subunit | Nucleotides in Oligonucleotide Tag | | |
|---|---|---|---|
| | (12–60) | (18–40) | (25–40) |
| 3 | 4–20 subunits | 6–13 subunits | 8–13 subunits |
| 4 | 3–15 subunits | 4–10 subunits | 6–10 subunits |
| 5 | 2–12 subunits | 3–8 subunits | 5–8 subunits |
| 6 | 2–10 subunits | 3–6 subunits | 4–6 subunits |

Most preferably, oligonucleotide tags are single stranded and specific hybridization occurs via Watson-Crick pairing with a tag complement.

Preferably, repertoires of single stranded oligonucleotide tags of the invention contain at least 100 members; more preferably, repertoires of such tags contain at least 1000 members; and most preferably, repertoires of such tags contain at least 10,000 members.

Triplex Tags

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Roberts et al, Proc. Natl. Acad. Sci., 93: 4320–4325 (1996); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267:5712–5721 (1992); Yoon et al, Proc. Natl. Acad. Sci., 89: 3840–3844 (1992); Blume et al, Nucleic Acids Research, 20: 1777–1784 (1992); Thuong and Helene, Angew. Chem. Int. Ed. Engl. 32: 666–690 (1993); Escude et al, Proc. Natl. Acad. Sci., 93: 4365–4369 (1996); and the like. Conditions for annealing single-stranded or duplex tags to their single-stranded or duplex complements are well known, e.g. Ji et al, Anal. Chem. 65: 1323–1328 (1993); Cantor et al, U.S. Pat. No. 5,482,836; and the like. Use of triplex tags has the advantage of not requiring a "stripping" reaction with polymerase to expose the tag for annealing to its complement.

Preferably, oligonucleotide tags of the invention employing triplex hybridization are double stranded DNA and the corresponding tag complements are single stranded. More preferably, 5-methylcytosine is used in place of cytosine in the tag complements in order to broaden the range of pH stability of the triplex formed between a tag and its complement. Preferred conditions for forming triplexes are fully disclosed in the above references. Briefly, hybridization takes place in concentrated salt solution, e.g. 1.0 M NaCl, 1.0 M potassium acetate, or the like, at pH below 5.5 (or 6.5 if 5-methylcytosine is employed). Hybridization temperature depends on the length and composition of the tag; however, for an 18–20-mer tag of longer, hybridization at room temperature is adequate. Washes may be conducted with less concentrated salt solutions, e.g. 10 mM sodium acetate, 100 mM $MgCl_2$, pH 5.8, at room temperature. Tags may be eluted from their tag complements by incubation in a similar salt solution at pH 9.0.

Minimally cross-hybridizing sets of oligonucleotide tags that form triplexes may be generated by the computer program of Appendix Ic, or similar programs. An exemplary set of double stranded 8-mer words are listed below in capital letters with the corresponding complements in small letters. Each such word differs from each of the other words in the set by three base pairs.

Table V

Exemplary Minimally Cross-Hybridizing Set of DoubleStranded 8-mer Tags

| | | | |
|---|---|---|---|
| 5'-AAGGAGAG | 5'-AAAGGGGA | 5'-AGAGAAGA | 5'-AGGGGGGG |
| 3'-TTCCTCTC | 3'-TTTCCCCT | 3'-TCTCTTCT | 3'-TCCCCCCC |
| 3'-ttcctctc | 3'-tttccccct | 3'-tctcttct | 3'-tccccccc |
| 5'-AAAAAAAA | 5'-AAGAGAGA | 5'-AGGAAAAG | 5'-GAAAGGAG |
| 3'-TTTTTTTT | 3'-TTCTCTCT | 3'-TCCTTTTC | 3'-CTTTCCTC |
| 3'-tttttttt | 3'-ttctctct | 3'-tccttttc | 3'-ctttcctc |
| 5'-AAAAAGGG | 5'-AGAAGAGG | 5'-AGGAAGGA | 5'-GAAGAAGG |
| 3'-TTTTTCCC | 3'-TCTTCTCC | 3'-TCCTTCCT | 3'-CTTCTTCC |
| 3'-tttttccc | 3'-tcttctcc | 3'-tccttcct | 3'-cttcttcc |
| 5'-AAAGGAAG | 5'-AGAAGGAA | 5'-AGGGGAAA | 5'-GAAGAGAA |
| 3'-TTTCCTTC | 3'-TCTTCCTT | 3'-TCCCCTTT | 3'-CTTCTCTT |
| 3'-tttccttc | 3'-tcttcctt | 3'-tcccctttt | 3'-cttctctt |

TABLE VI

Repertoire Size of Various Double Stranded Tags That Form Triplexes with Their Tag Complements

| Oligo-nucleotide Word Length | Nucleotide Difference between Oligonucleotides of Minimally Cross-Hybridizing Set | Maximal Size of Minimally Cross-Hybridizing Set | Size of Repertoire with Four Words | Size of Repertoire with Five Words |
|---|---|---|---|---|
| 4 | 2 | 8 | 4096 | $3.2 \times 10^4$ |
| 6 | 3 | 8 | 4096 | $3.2 \times 10^4$ |
| 8 | 3 | 16 | $6.5 \times 10^4$ | $1.05 \times 10^6$ |
| 10 | 5 | 8 | 4096 | |
| 15 | 5 | 92 | | |
| 20 | 6 | 765 | | |

TABLE VI-continued

Repertoire Size of Various Double Stranded Tags That Form Triplexes with Their Tag Complements

| Oligo-nucleotide Word Length | Nucleotide Difference between Oligonucleotides of Minimally Cross-Hybridizing Set | Maximal Size of Minimally Cross-Hybridizing Set | Size of Repertoire with Four Words | Size of Repertoire with Five Words |
|---|---|---|---|---|
| 20 | 8 | 92 | | |
| 20 | 10 | 22 | | |

Preferably, repertoires of double stranded oligonucleotide tags of the invention contain at least 10 members; more preferably, repertoires of such tags contain at least 100 members. Preferably, words are between 4 and 8 nucleotides in length for combinatorially synthesized double stranded oligonucletide tags, and oligonucleotide tags are between 12 and 60, 12 to 30, or 15 to 24 base pairs in length. More preferably, such tags are between 18 and 40 base pairs in length.

Solid Phase Supports

Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles are employed such that each has a uniform coating, or population, of complementary sequences of the same tag (and no other), or a single or a few supports are employed with spatially discrete regions each containing a uniform coating, or population, of complementary sequences to the same tag (and no other). In the latter embodiment, the area of the regions may vary according to particular applications; usually, the regions range in area from several $\mu m^2$, e.g. 3–5, to several hundred $\mu m^2$, e.g. 100–500 or e.g. 10 to 1000 micrometers$^2$. Preferably, such regions are spatially discrete so that signals generated by events, e.g. fluorescent emissions, at adjacent regions can be resolved by the detection system being employed. In some applications, it may be desirable to have regions with uniform coatings of more than one tag complement, e.g. for simultaneous sequence analysis, or for bringing separately tagged molecules into close proximity.

Tag complements may be used with the solid phase support that they are synthesized on, or they may be separately synthesized and attached to a solid phase support for use, e.g. as disclosed by Lund et al, Nucleic Acids Research, 16: 10861–10880 (1988); Albretsen et al, Anal. Biochem., 189: 40–50 (1990); Wolf et al, Nucleic Acids Research, 15: 2911–2926 (1987); or Ghosh et al, Nucleic Acids Research, 15: 5353–5372 (1987). Preferably, tag complements are synthesized on and used with the same solid phase support, which may comprise a variety of forms and include a variety of linking moieties. Such supports may comprise microparticles or arrays, or matrices, of regions where uniform populations of tag complements are synthesized. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678, 814; 4,413,070; and 4,046;720; and Pon, Chapter 19, in Agrawal, editor, Methods in Molecular Biology, Vol. 20, (Humana Press, Totowa, N.J., 1993). Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on the conditions under which the tags are used. For example, in applications involving successive processing with enzymes, supports and linkers that minimize steric hindrance of the enzymes and that facilitate access to substrate are preferred. Other important factors to be considered in selecting the most appropriate microparticle support include size uniformity, efficiency as a synthesis support, degree to which surface area known, and optical properties, e.g. as explain more fully below, clear smooth beads provide instrumentational advantages when handling large numbers of beads on a surface.

Exemplary linking moieties for attaching and/or synthesizing tags on microparticle surfaces are disclosed in Pon et al, Biotechniques, 6:768–775 (1988); Webb, U.S. Pat. No. 4,659,774; Barany et al, International patent application PCT/US91/06103; Brown et al, J. Chem. Soc. Commun., 1989: 891–893; Damha et al, Nucleic Acids Research, 18: 3813–3821 (1990); Beattie et al, Clinical Chemistry, 39: 719–722 (1993); Maskos and Southern, Nucleic Acids Research, 20: 1679–1684 (1992); and the like.

As mentioned above, tag complements may also be synthesized on a single (or a few) solid phase support to form an array of regions uniformly coated with tag complements. That is, within each region in such an array the same tag complement is synthesized. Techniques for synthesizing such arrays are disclosed in McGall et al, International application PCT/US93/03767; Pease et al, Proc. Natl. Acad. Sci., 91: 5022–5026 (1994); Southern and Maskos, International application PCT/GB89/01114; Maskos and Southern (cited above); Southern et al, Genomics, 13: 1008–1017 (1992); and Maskos and Southern, Nucleic Acids Research, 21: 4663–4669 (1993).

Preferably, the invention is implemented with microparticles or beads uniformly coated with complements of the same tag sequence. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1–2, to several hundred, e.g. 200–1000 µm diameter are preferable, as they facilitate the construction and manipulation of large repertoires of oligonucleotide tags with minimal reagent and sample usage.

In some preferred applications, commercially available controlled-pore glass (CPG) or polystyrene supports are employed as solid phase supports in the invention. Such supports come available with base-labile linkers and initial nucleosides attached, e.g. Applied Biosystems (Foster City, Calif.). Preferably, microparticles having pore size between 500 and 1000 angstroms are employed.

In other preferred applications, non-porous microparticles are employed for their optical properties, which may be advantageously used when tracking large numbers of microparticles on planar supports, such as a microscope slide. Particularly preferred non-porous microparticles are the glycidal methacrylate (GMA) beads available from Bangs Laboratories (Carmel, Ind.). Such microparticles are useful in a variety of sizes and derivatized with a variety of linkage groups for synthesizing tags or tag complements. Preferably, for massively parallel manipulations of tagged microparticles, 5 µm diameter GMA beads are employed.

Attaching Tags to Polynucleotides For Sorting onto Solid Phase Supports

An important aspect of the invention is the sorting and attachment of a populations of polynucleotides, e.g. from a cDNA library, to microparticles or to separate regions on a solid phase support such that each microparticle or region has substantially only one kind of polynucleotide attached. This objective is accomplished by insuring that substantially all different polynucleotides have different tags attached. This condition, in turn, is brought about by taking a sample of the full ensemble of tag-polynucleotide conjugates for analysis. (It is acceptable that identical polynucleotides have different tags, as it merely results in the same polynucleotide being operated on or analyzed twice in two different locations.) Such sampling can be carried out either overtly—for example, by taking a small volume from a larger mixture—after the tags have been attached to the polynucleotides, it can be carried out inherently as a secondary effect of the techniques used to process the polynucleotides and tags, or sampling can be carried out both overtly and as an inherent part of processing steps.

Preferably, in constructing a cDNA library where substantially all different cDNAs have different tags, a tag repertoire is employed whose complexity, or number of distinct tags, greatly exceeds the total number of mRNAs extracted from a cell or tissue sample. Preferably, the complexity of the tag repertoire is at least 10 times that of the polynucleotide population; and more preferably, the complexity of the tag repertoire is at least 100 times that of the polynucleotide population. Below, a protocol is disclosed for cDNA library construction using a primer mixture that contains a full repertoire of exemplary 9-word tags. Such a mixture of tag-containing primers has a complexity of $8^9$, or about $1.34 \times 10^8$. As indicated by Winslow et al, Nucleic Acids Research, 19: 3251–3253 (1991), mRNA for library construction can be extracted from as few as 10–100 mammalian cells. Since a single mammalian cell contains about $5 \times 10^5$ copies of mRNA molecules of about $3.4 \times 10^4$ different kinds, by standard techniques one can isolate the MRNA from about 100 cells, or (theoretically) about $5 \times 10^7$ mRNA molecules. Comparing this number to the complexity of the primer mixture shows that without any additional steps, and even assuming that mRNAs are converted into cDNAs with perfect efficiency (1% efficiency or less is more accurate), the cDNA library construction protocol results in a population containing no more than 37% of the total number of different tags. That is, without any overt sampling step at all, the protocol inherently generates a sample that comprises 37%, or less, of the tag repertoire. The probability of obtaining a double under these conditions is about 5%, which is within the preferred range. With mRNA from 10 cells, the fraction of the tag repertoire sampled is reduced to only 3.7%, even assuming that all the processing steps take place at 100% efficiency. In fact, the efficiencies of the processing steps for constructing cDNA libraries are very low, a "rule of thumb" being that good library should contain about $10^8$ cDNA clones from mRNA extracted from $10^6$ mammalian cells.

Use of larger amounts of mRNA in the above protocol, or for larger amounts of polynucleotides in general, where the number of such molecules exceeds the complexity of the tag repertoire, a tag-polynucleotide conjugate mixture potentially contains every possible pairing of tags and types of mRNA or polynucleotide. In such cases, overt sampling may be implemented by removing a sample volume after a serial dilution of the starting mixture of tag-polynucleotide conjugates. The amount of dilution required depends on the amount of starting material and the efficiencies of the processing steps, which are readily estimated.

If mRNA were extracted from $10^6$ cells (which would correspond to about 0.5 µg of poly(A)$^+$ RNA), and if primers were present in about 10–100 fold concentration excess—as is called for in a typical protocol, e.g. Sambrook et al, Molecular Cloning, Second Edition, page 8.61 [10 µL 1.8 kb mRNA at 1 mg/mL equals about $1.68 \times 10^{-11}$ moles and 10 µL 18-mer primer at 1 mg/niL equals about $1.68 \times 10^{-9}$ moles], then the total number of tag-polynucleotide conjugates in a cDNA library would simply be equal to or less than the starting number of mRNAs, or about $5 \times 10^{11}$ vectors containing tag-polynucleotide conjugates—again this assumes that each step in cDNA construction—first strand synthesis, second strand synthesis, ligation into a vector—occurs with perfect efficiency, which is a very conservative estimate. The actual number is significantly less.

If a sample of n tag-polynucleotide conjugates are randomly drawn from a reaction mixture—as could be effected by taking a sample volume, the probability of drawing conjugates having the same tag is described by the Poisson distribution, $P(r)=e^{-\lambda}(\lambda)^r/r$, where r is the number of conjugates having the same tag and $\lambda$=np, where p is the probability of a given tag being selected. If n=$10^6$ and p=1/(1.34× $10^8$), then $\lambda$=0.00746 and P(2)=$2.76 \times 10^{-5}$. Thus, a sample of one million molecules gives rise to an expected number of doubles well within the preferred range. Such a sample is readily obtained as follows: Assume that the $5 \times 10^{11}$ mRNAs are perfectly converted into $5 \times 10^{11}$ vectors with tag-cDNA conjugates as inserts and that the $5 \times 10^{11}$ vectors are in a reaction solution having a volume of 100 µL. Four 10-fold serial dilutions may be carried out by transferring 10 µl from the original solution into a vessel containing 90 µl of an appropriate buffer, such as TE. This process may be repeated for three additional dilutions to obtain a 100 µl solution containing $5 \times 10^5$ vector molecules per µl. A 2 µl aliquot from this solution yields $10^6$ vectors containing tag-cDNA conjugates as inserts. This sample is then amplified by straight forward transformation of a competent host cell followed by culturing.

Of course, as mentioned above, no step in the above process proceeds with perfect efficiency. In particular, when vectors are employed to amplify a sample of tag-polynucleotide conjugates, the step of transforming a host is very inefficient. Usually, no more than 1% of the vectors are taken up by the host and replicated. Thus, for such a method of amplification, even fewer dilutions would be required to obtain a sample of $10^6$ conjugates.

A repertoire of oligonucleotide tags can be conjugated to a population of polynucleotides in a number of ways, including direct enzymatic ligation, amplification, e.g. via PCR, using primers containing the tag sequences, and the like.

The initial ligating step produces a very large population of tag-polynucleotide conjugates such that a single tag is generally attached to many different polynucleotides. However, as noted above, by taking a sufficiently small sample of the conjugates, the probability of obtaining "doubles," i.e. the same tag on two different polynucleotides, can be made negligible. Generally, the larger the sample the greater the probability of obtaining a double. Thus, a design trade-off exists between selecting a large sample of tag-polynucleotide conjugates—which, for example, ensures adequate coverage of a target polynucleotide in a shotgun sequencing operation or adequate representation of a rapidly changing mRNA pool, and selecting a small sample which ensures that a minimal number of doubles will be present. In most embodiments, the presence of doubles merely adds an additional source of noise or, in the case of sequencing, a minor complication in scanning and signal processing, as microparticles giving multiple fluorescent signals can simply be ignored.

As used herein, the term "substantially all" in reference to attaching tags to molecules, especially polynucleotides, is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the polynucleotides have unique tags attached. More preferably, it means that at least ninety percent of the polynucleotides have unique tags attached. Still more preferably, it means that at least ninety-five percent of the polynucleotides have unique tags attached. And, most preferably, it means that at least ninety-nine percent of the polynucleotides have unique tags attached.

Preferably, when the population of polynucleotides consists of messenger RNA (mRNA), oligonucleotides tags may be attached by reverse transcribing the mRNA with a set of primers preferably containing complements of tag sequences. An exemplary set of such primers could have the following sequence (SEQ ID NO:1):

5'-mRNA-[A]$_n$-3'[T]$_{19}$GG[W,W,W,C]$_9$ACCAGCTGATC-5'-biotin where "[W,W,W,C]$_9$" represents the sequence of an oligonucleotide tag of nine subunits of four nucleotides each and "[W,W,W,C]" represents the subunit sequences listed above, i.e. "W" represents T or A. The underlined sequences identify an optional restriction endonuclease site that can be used to release the polynucleotide from attachment to a solid phase support via the biotin, if one is employed. For the above primer, the complement attached to a microparticle could have the form (SEQ ID NO:2):

5'-[G,W,W,W]$_9$TGG-linker-microparticle

After reverse transcription, the mRNA is removed, e.g. by RNase H digestion, and the second strand of the cDNA is synthesized using, for example, a primer of the following form (SEQ ID NO:3):

5'-NRRGATCYNNN-3' where N is any one of A, T, G, or C; R is a purine-containing nucleotide, and Y is a pyrimidine-containing nucleotide. This particular primer creates a Bst Y1 restriction site in the resulting double stranded DNA which, together with the Sal I site, facilitates cloning into a vector with, for example, Bam HI and Xho I sites. After Bst Y1 and Sal I digestion, the exemplary conjugate would have the form (SEQ ID NO:4):

5'-RCGACCA[C,W,W,W]$_9$GG[T]$_{19}$-cDNA-NNNR GGT [G,W,W,W]$_9$CC[A]$_{19}$-rDNA-NNNYCTAG-5'

The polynucleotide-tag conjugates may then be manipulated using standard molecular biology techniques. For example, the above conjugate-which is actually a mixture—may be inserted into commercially available cloning vectors, e.g. Stratagene Cloning System (La Jolla, Calif.); transfected into a host, such as a commercially available host bacteria; which is then cultured to increase the number of conjugates. The cloning vectors may then be isolated using standard techniques, e.g. Sambrook et al, Molecular Cloning, Second Edition (Cold Spring Harbor Laboratory, New York, 1989). Alternatively, appropriate adaptors and primers may be employed so that the conjugate population can be increased by PCR.

Preferably, when the ligase-based method of sequencing is employed, the Bst Y1 and Sal I digested fragments are cloned into a Bam HI-/Xho I-digested vector having the following single-copy restriction sites (SEQ ID NO:5):

5'-GAGGATGCCTTTATTCCACTCGAGATCCAA
TCCA-3'FokI BamHI XhoI

This adds the Fok I site which will allow initiation of the sequencing process discussed more fully below.

Tags can be conjugated to cDNAs of existing libraries by standard cloning methods. cDNAs are excised from their existing vector, isolated, and then ligated into a vector containing a repertoire of tags. Preferably, the tag-containing vector is linearized by cleaving with two restriction enzymes so that the excised cDNAs can be ligated in a predetermined orientation. The concentration of the linearized tag-containing vector is in substantial excess over that of the cDNA inserts so that ligation provides an inherent sampling of tags.

A general method for exposing the single stranded tag after amplification involves digesting a target polynucleotide-containing conjugate with the 3'→5' exonuclease activity of T4 DNA polymerase, or a like enzyme. When used in the presence of a single deoxynucleoside triphosphate, such a polymerase will cleave nucleotides from 3' recessed ends present on the non-template strand of a double stranded fragment until a complement of the single deoxynucleoside triphosphate is reached on the template strand. When such a nucleotide is reached the 3'→5' digestion effectively ceases, as the polymerase's extension activity adds nucleotides at a higher rate than the excision activity removes nucleotides. Consequently, single stranded tags constructed with three nucleotides are readily prepared for loading onto solid phase supports.

The technique may also be used to preferentially methylate interior Fok I sites of a target polynucleotide while leaving a single Fok I site at the terminus of the palynucleotide unmethylated. First, the terminal Fok I site is rendered single stranded using a polymerase with deoxycytidine triphosphate. The double stranded portion of the fragment is then methylated, after which the single stranded terminus is filled in with a DNA polymerase in the presence of all four nucleoside triphosphates, thereby regenerating the Fok I site. Clearly, this procedure can be generalized to endonucleases other than Fok I.

After the oligonucleotide tags are prepared for specific hybridization, e.g. by rendering them single stranded as described above, the polynucleotides are mixed with microparticles containing the complementary sequences of the tags under conditions that favor the formation of perfectly matched duplexes between the tags and their complements. There is extensive guidance in the literature for creating these conditions. Exemplary references providing such guidance include Wetmur, Critical Reviews in Biochemistry and Molecular Biology, 26: 227–259 (1991); Sambrook et al, Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags may be ligated to the complementary sequences attached to the microparticles. Finally, the microparticles are washed to remove polynucleotides with unligated and/or mismatched tags.

When CPG microparticles conventionally employed as synthesis supports are used, the density of tag complements on the microparticle surface is typically greater than that necessary for some sequencing operations. That is, in sequencing approaches that require successive treatment of the attached polynucleotides with a variety of enzymes, densely spaced polynucleotides may tend to inhibit access of the relatively bulky enzymes to the polynucleotides. In such cases, the polynucleotides are preferably mixed with the microparticles so that tag complements are present in significant excess, e.g. from 10:1 to 100:1, or greater, over the polynucleotides. This ensures that the density of polynucleotides on the microparticle surface will not be so high as to inhibit enzyme access. Preferably, the average inter-polynucleotide spacing on the microparticle surface is on the order of 30–100 nm. Guidance in selecting ratios for standard CPG supports and Ballotini beads (a type of solid glass support) is found in Maskos and Southern, Nucleic Acids Research, 20: 1679–1684 (1992). Preferably, for sequencing applications, standard CPG beads of diameter in the range of 20–50 $\mu$m are loaded with about $10^5$ polynucleotides, and GMA beads of diameter in the range of 5–10 $\mu$m are loaded with a few tens of thousand polynucleotide, e.g. $4\times10^4$ to $6\times10^4$.

In the preferred embodiment, tag complements are synthesized on microparticles combinatorially; thus, at the end of the synthesis, one obtains a complex mixture of microparticles from which a sample is taken for loading tagged polynucleotides. The size of the sample of microparticles will depend on several factors, including the size of the repertoire of tag complements, the nature of the apparatus for used for observing loaded microparticles—e.g. its capacity, the tolerance for multiple copies of microparticles with the same tag complement (i.e. "bead doubles"), and the like. The following table provide guidance regarding microparticle sample size, microparticle diameter, and the approximate physical imensions of a packed array of microparticles of various diameters.

| Microparticle diameter | 5 $\mu$m | 10 $\mu$m | 20 $\mu$m | 40 $\mu$m |
|---|---|---|---|---|
| Max. no. polynucleotides loaded at 1 per $10^5$ sq. angstrom | | $3 \times 10^5$ | $1.26 \times 10^6$ | $5 \times 10^6$ |
| Approx. area of monolayer of $10^6$ microparticles | .45 × .45 cm | 1 × 1 cm | 2 × 2 cm | 4 × 4 cm |

The probability that the sample of microparticles contains a given tag complement or is present in multiple copies is described by the Poisson distribution, as indicated in the following table.

TABLE VII

| Number of microparticles in sample (as fraction of repertoire size), m | Fraction of repertoire of tag complements present in sample, $1-e^{-m}$ | Fraction of microparticles in sample with unique tag complement attached, $m(e^{-m})/2$ | Fraction of microparticles in sample carrying same tag complement as one other microparticle in sample ("bead doubles"), $m^2(e^{-m})/2$ |
|---|---|---|---|
| 1.000 | 0.63 | 0.37 | 0.18 |
| .693 | 0.50 | 0.35 | 0.12 |
| .405 | 0.33 | 0.27 | 0.05 |
| .285 | 0.25 | 0.21 | 0.03 |
| .223 | 0.20 | 0.18 | 0.02 |
| .105 | 0.10 | 0.09 | 0.005 |
| .010 | 0.01 | 0.01 | |

High Specificity Sorting and Panning

The kinetics of sorting depends on the rate of hybridization of oligonucleotide tags to their tag complements which, in turn, depends on the complexity of the tags in the hybridization reaction. Thus, a trade off exists between sorting rate and tag complexity, such that an increase in sorting rate may be achieved at the cost of reducing the complexity of the tags involved in the hybridization reaction. As explained below, the effects of this trade off may be ameliorated by "panning."

Specificity of the hybridizations may be increased by taking a sufficiently small sample so that both a high percentage of tags in the sample are unique and the nearest neighbors of substantially all the tags in a sample differ by at least two words. This latter condition may be met by taking a sample that contains a number of tag-polynucleotide conjugates that is about 0.1 percent or less of the size of the repertoire being employed. For example, if tags are constructed with eight words selected from Table II, a repertoire of $8^8$, or about $1.67 \times 10^7$, tags and tag complements are produced. In a library of tag-cDNA conjugates as described above, a 0.1 percent sample means that about 16,700 different tags are present. If this were loaded directly onto a repertoire-equivalent of microparticles, or in this example a sample of $1.67 \times 10^7$ microparticles, then only a sparse subset of the sampled microparticles would be loaded. The density of loaded microparticles can be increase—for example, for more efficient sequencing—by undertaking a "panning" step in which the sampled tag-cDNA conjugates are used to separate loaded microparticles from unloaded microparticles. Thus, in the example above, even though a "0.1 percent" sample contains only 16,700 cDNAs, the sampling and panning steps may be repeated until as many loaded microparticles as desired are accumulated.

A panning step may be implemented by providing a sample of tag-cDNA conjugates each of which contains a capture moiety at an end opposite, or distal to, the oligonucleotide tag. Preferably, the capture moiety is of a type which can be released from the tag-cDNA conjugates, so that the tag-cDNA conjugates can be sequenced with a single-base sequencing method. Such moieties may comprise biotin, digoxigenin, or like ligands, a triplex binding region, or the like. Preferably, such a capture moiety comprises a biotin component. Biotin may be attached to tag-cDNA conjugates by a number of standard techniques. If appropriate adapters containing PCR primer binding sites are attached to tag-cDNA conjugates, biotin may be attached by using a biotinylated primer in an amplification after sampling.

Alternatively, if the tag-cDNA conjugates are inserts of cloning vectors, biotin may be attached after excising the tag-cDNA conjugates by digestion with an appropriate restriction enzyme followed by isolation and filling in a protruding strand distal to the tags with a DNA polymerase in the presence of biotinylated uridine triphosphate.

After a tag-cDNA conjugate is captured, it may be released from the biotin moiety in a number of ways, such as by a chemical linkage that is cleaved by reduction, e.g. Herman et al, Anal. Biochem., 156: 48–55 (1986), or that is cleaved photochemically, e.g. Olejnik et al, Nucleic Acids Research, 24: 361–366 (1996), or that is cleaved enzymatically by introducing a restriction site in the PCR primer. The latter embodiment can be exemplified by considering the library of tag-polynucleotide conjugates described above (SEQ ID NO:4):

5'-RCGACCA[C,W,W,W]$_9$GG[T]$_{19}$-cDNA-NNNR GGT [G,W,W,W]$_9$CC[A]$_{19}$-rDNA-NNNYCTAG-5'

The following adapters may be ligated to the ends of these fragments to permit amplification by PCR:

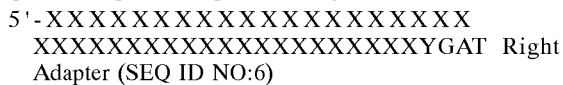
Right Adapter (SEQ ID NO:6)

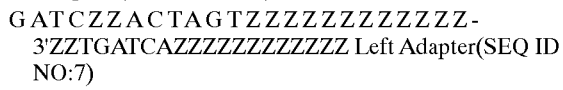
Left Adapter(SEQ ID NO:7)

-5'-biotin Left Primer (SEQ ID NO:8)

where "ACTAGT" is a Spe I recognition site (which leaves a staggered cleavage ready for single base sequencing), and the X's and Z's are nucleotides selected so that the annealing and dissociation temperatures of the respective primers are approximately the same. After ligation of the adapters and amplification by PCR using the biotinylated primer, the tags of the conjugates are rendered single stranded by the exonuclease activity of T4 DNA polymerase and conjugates are combined with a sample of microparticles, e.g. a repertoire equivalent, with tag complements attached. After annealing under stringent conditions (to minimize mis-attachment of tags), the conjugates are preferably ligated to their tag complements and the loaded microparticles are separated from the unloaded microparticles by capture with avidinated magnetic beads, or like capture technique.

Returning to the example, this process results in the accumulation of about 10,500 (=16,700×0.63) loaded microparticles with different tags, which may be released from the magnetic beads by cleavage with Spe I. By repeating this process 40–50 times with new samples of microparticles and tag-cDNA conjugates, 4–5×10$^5$ cDNAs can be accumulated by pooling the released microparticles. The pooled microparticles may then be simultaneously sequenced by a single-base sequencing technique.

Determining how many times to repeat the sampling and panning steps—or more generally, determining how many cDNAs to analyze, depends on one's objective. If the objective is to monitor the changes in abundance of relatively common sequences, e.g. making up 5% or more of a population, then relatively small samples, i.e. a small fraction of the total population size, may allow statistically significant estimates of relative abundances. On the other hand, if one seeks to monitor the abundances of rare sequences, e.g. making up 0.1% or less of a population, then large samples are required. Generally, there is a direct relationship between sample size and the reliability of the estimates of relative abundances based on the sample. There is extensive guidance in the literature on determining appropriate sample sizes for making reliable statistical estimates, e.g. Koller et al, Nucleic Acids Research, 23:185–191 (1994); Good, Biometrika, 40: 16–264 (1953); Bunge et al, J. Am. Stat. Assoc., 88: 364–373 (1993); and the like. Preferably, for monitoring changes in gene expression based on the analysis of a series of cDNA libraries containing $10^5$ to $10^8$ independent clones of $3.0–3.5\times10^4$ different sequences, a sample of at least $10^4$ sequences are accumulated for analysis of each library. More preferably, a sample of at least $10^5$ sequences are accumulated for the analysis of each library; and most preferably, a sample of at least $5\times10^5$ sequences are accumulated for the analysis of each library. Alternatively, the number of sequences sampled is prefer- ably sufficient to estimate the relative abundance of a sequence present at a frequency within the range of 0.1% to 5% with a 95% confidence limit no larger than 0.1% of the population size.

strand of the polynucleotide by the identity of the ligated probe; (d) cleaving the ligated complex with a nuclease; and (e) repeating steps (a) through (d) until the nucleotide sequence of the polynucleotide, or a portion thereof, is determined.

A single signal generating moiety, such as a single fluorescent dye, may be employed when sequencing several different target polynucleotides attached to different spatially addressable solid phase supports, such as fixed microparticles, in a parallel sequencing operation. This may be accomplished by providing four sets of probes that are applied sequentially to the plurality of target polynucleotides on the different microparticles. An exemplary set of such probes are shown below:

| Set1 | Set2 | Set3 | Set4 |
|---|---|---|---|
| ANNNN...NN<br>N...NNTT...T* | dANNNN...NN<br>d N...NNTT...T | dANNNN...NN<br>N...NNTT...T | dANNNN...NN<br>N...NNTT...T |
| dCNNNN...NN<br>N...NNTT...T | CNNNN...NN<br>N...NNTT...T* | dCNNNN...NN<br>N...NNTT...T | dCNNNN...NN<br>N...NNTT...T |
| dGNNNN...NN<br>N...NNTT...T | dGNNNN...NN<br>N...NNTT...T | GNNNN...NN<br>N...NNTT...T* | dGNNNN...NN<br>N...NNTT...T |
| dTNNNN...NN<br>N...NNTT...T | dTNNNN...NN<br>N...NNTT...T | dTNNNN...NN<br>N...NNTT...T | TNNNN...NN<br>N...NNTT...T* | where each of the listed probes represents a mixture of $4^3=64$ oligonucleotides such that the identity of the 3' terminal nucleotide of the top strand is fixed and the other positions in the protruding strand are filled by every 3-mer permutation of nucleotides, or complexity reducing analogs. The listed probes are also shown with a single stranded poly-T tail with a signal generating moiety attached to the terminal thyrndine, shown as "T*". The "d" on the unlabeled probes designates a ligation-blocking moiety or absense of 3'-hydroxyl, which prevents unlabeled probes from being ligated. Preferably, such 3'-terminal nucleotides are dideoxynucleotides. In this embodiment, the probes of set 1 are first applied to the plurality of target polynucleotides and treated with a ligase so that target polynucleotides having a thymidine complementary to the 3' terminal adenosine of the labeled probes are ligated. The unlabeled probes are simultaneously applied to minimize inappropriate ligations. The locations of the target polynucleotides that form ligated complexes with probes terminating in "A" are identified by the signal generated by the label carried on the probe. After washing and cleavage, the probes of set 2 are applied. In this case, target polynucleotides forming ligated complexes with probes terminating in "C" are identified by location. Similarly, the probes of sets 3 and 4 are applied and locations of positive signals identified. This process of sequentially applying the four sets of probes continues until the desired number of nucleotides are identified on the target polynucleotides. Clearly, one of ordinary skill could construct similar sets of probes that could have many variations, such as having protruding strands of different lengths, different moieties to block ligation of unlabeled probes, different means for labeling probes, and the like.

Single Base DNA Sequencing

The present invention can be employed with conventional methods of DNA sequencing, e.g. as disclosed by Hultman et al, Nucleic Acids Research, 17: 4937–4946 (1989). However, for parallel, or simultaneous, sequencing of multiple polynucleotides, a DNA sequencing methodology is preferred that requires neither electrophoretic separation of closely sized DNA fragments nor analysis of cleaved nucleotides by a separate analytical procedure, as in peptide sequencing. Preferably, the methodology permits the step-wise identification of nucleotides, usually one at a time, in a sequence through successive cycles of treatment and detection. Such methodologies are referred to herein as "single base" sequencing methods. Single base approaches are disclosed in the following references: Cheeseman, U.S. Pat. No. 5,302,509; Tsien et al, International application WO 91/06678; Rosenthal et al, International application WO 93/21340; Canard et al, Gene, 148: 1–6 (1994); and Metzker et al, Nucleic Acids Research, 22: 4259–4267 (1994).

A "single base" method of DNA sequencing which is suitable for use with the present invention and which requires no electrophoretic separation of DNA fragments is described in International application PCT/US95/03678. Briefly, the method comprises the following steps: (a) ligating a probe to an end of the polynucleotide having a protruding strand to form a ligated complex, the probe having a complementary protruding strand to that of the polynucleotide and the probe having a nuclease recognition site; (b) removing unligated probe from the ligated complex; (c) identifying one or more nucleotides in the protruding

Apparatus for Observing Enzymatic Processes and/ or Binding Events at Microparticle Surfaces An objective of the invention is to sort identical molecules, particularly polynucleotides, onto the surfaces of microparticles by the specific hybridization of tags and their complements. Once such sorting has taken place, the presence of the molecules or operations performed on them can be detected in a number of ways depending on the nature of the tagged molecule, whether microparticles are detected separately or in "batches," whether repeated measurements are desired, and the like. Typically, the sorted molecules are exposed to ligands for binding, e.g. in drug development, or are subjected chemical or enzymatic processes, e.g. in polynucleotide sequencing. In both of these uses it is often desirable to simultaneously observe signals corresponding to such events or processes on large numbers of microparticles. Microparticles carrying sorted molecules (referred to herein as "loaded" microparticles) lend themselves to such large scale parallel operations, e.g. as demonstrated by Lam et al (cited above).

Preferably, whenever light-generating signals, e.g. chemiluminescent, fluorescent, or the like, are employed to detect events or processes, loaded microparticles are spread on a planar substrate, e.g. a glass slide, for examination with a scanning system, such as described in International patent applications PCT/US91/09217, PCT/NL90/00081, and PCT/US95/01886. The scanning system should be able to reproducibly scan the substrate and to define the positions of each microparticle in a predetermined region by way of a coordinate system. In polynucleotide sequencing applications, it is important that the positional identification of microparticles be repeatable in successive scan steps.

Such scanning systems may be constructed from commercially available components, e.g. x-y translation table controlled by a digital computer used with a detection system comprising one or more photomultiplier tubes, or alternatively, a CCD array, and appropriate optics, e.g. for exciting, collecting, and sorting fluorescent signals. In some embodiments a confocal optical system may be desirable. An exemplary scanning system suitable for use in four-color sequencing is illustrated diagrammatically in FIG. 2. Substrate 300, e.g. a microscope slide with fixed microparticles, is placed on x-y translation table 302, which is connected to and controlled by an appropriately prograrrmed digital computer 304 which may be any of a variety of commercially available personal computers, e.g. 486-based machines or PowerPC model 7100 or 8100 available form Apple Computer (Cupertino, Calif.). Computer software for table translation and data collection functions can be provided by commercially available laboratory software, such as Lab Windows, available from National Instruments.

Figure 2:
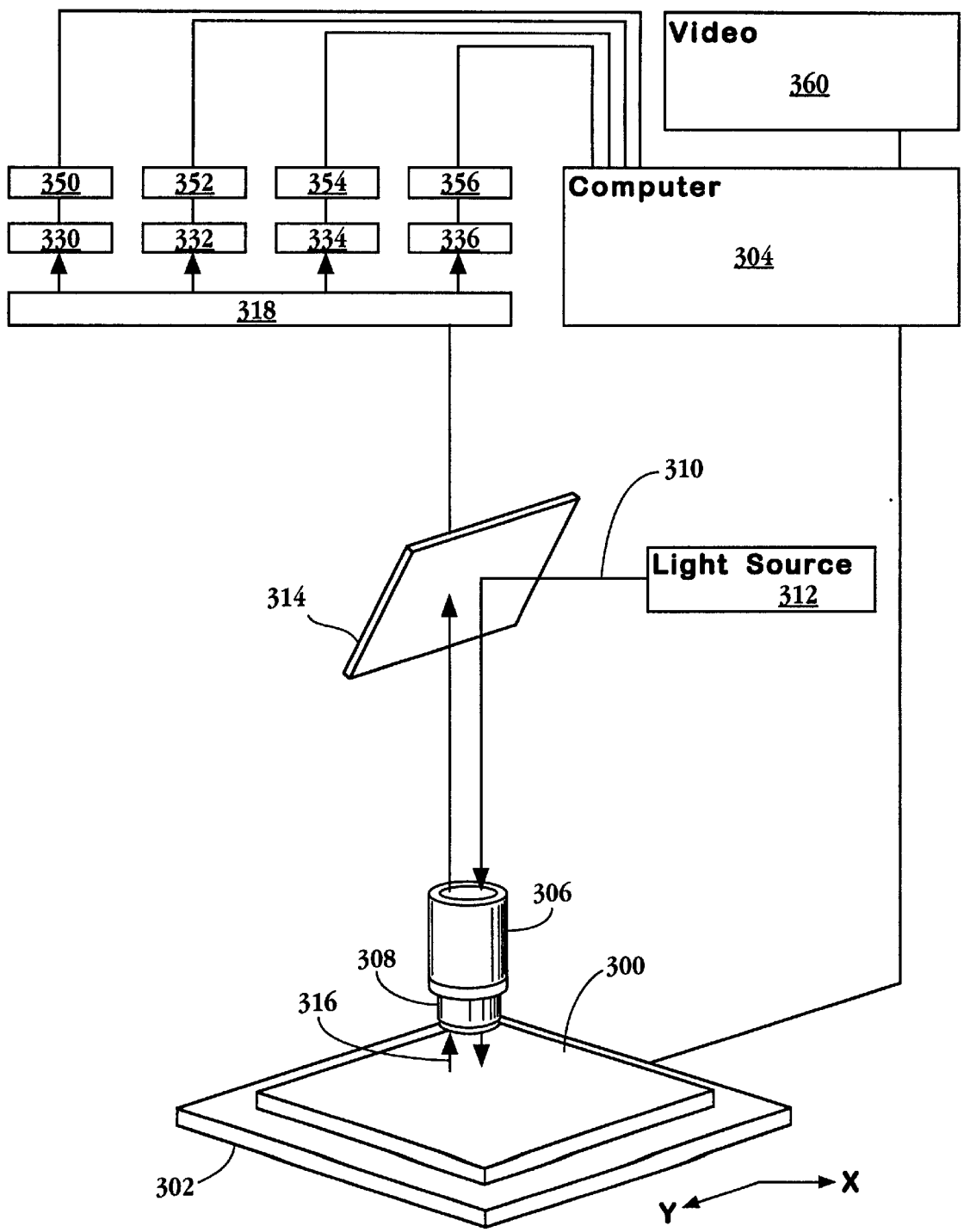
FIG. 2 diagrammatically illustrates an apparatus for carrying out parallel operations, such as polynucleotide sequencing, in accordance with the invention.

Substrate 300 and table 302 are operationally associated with microscope 306 having one or more objective lenses 308 which are capable of collecting and delivering light to microparticles fixed to substrate 300. Excitation beam 310 from light source 312, which is preferably a laser, is directed to beam splitter 314, e.g. a dichroic mirror, which re-directs the beam through microscope 306 and objective lens 308 which, in turn, focuses the beam onto substrate 300. Lens 308 collects fluorescence 316 emitted from the microparticles and directs it through beam splitter 314 to signal distribution optics 318 which, in turn, directs fluorescence to one or more suitable opto-electronic devices for converting some fluorescence characteristic, e.g. intensity, lifetime, or the like, to an electrical signal. Signal distribution optics 318 may comprise a variety of components standard in the art, such as bandpass filters, fiber optics, rotating mirrors, fixed position mirrors and lenses, diffraction gratings, and the like. As illustrated in FIG. 2, signal distribution optics 318 directs fluorescence 316 to four separate photomultiplier tubes, 330, 332, 334, and 336, whose output is then directed to pre-amps and photon counters 350, 352, 354, and 356. The output of the photon counters is collected by computer 304, where it can be stored, analyzed, and viewed on video 360. Alternatively, signal distribution optics 318 could be a diffraction grating which directs fluorescent signal 318 onto a CCD array.

The stability and reproducibility of the positional localization in scanning will determine, to a large extent, the resolution for separating closely spaced microparticles. Preferably, the scanning systems should be capable of resolving closely spaced microparticles, e.g. separated by a particle diameter or less. Thus, for most applications, e.g. using CPG microparticles, the scanning system should at least have the capability of resolving objects on the order of 10–100 $\mu$m. Even higher resolution may be desirable in some embodiments, but with increase resolution, the time required to fully scan a substrate will increase; thus, in some embodiments a compromise may have to be made between speed and resolution. Increases in scanning time can be achieved by a system which only scans positions where microparticles are known to be located, e.g from an initial full scan. Preferably, microparticle size and scanning system resolution are selected to permit resolution of fluorescently labeled microparticles randomly disposed on a plane at a density between about ten thousand to one hundred thousand microparticles per $cm^2$.

In sequencing applications, loaded microparticles can be fixed to the surface of a substrate in variety of ways. The fixation should be strong enough to allow the microparticles to undergo successive cycles of reagent exposure and washing without significant loss. When the substrate is glass, its surface may be derivatized with an alkylamino linker using commercially available reagents, e.g. Pierce Chemical, which in turn may be cross-linked to avidin, again using conventional chemistries, to form an avidinated surface. Biotin moieties can be introduced to the loaded microparticles in a number of ways. For example, a fraction, e.g. 10–15 percent, of the cloning vectors used to attach tags to polynucleotides are engineered to contain a unique restriction site (providing sticky ends on digestion) immediately adjacent to the polynucleotide insert at an end of the polynucleotide opposite of the tag. The site is excised with the polynucleotide and tag for loading onto microparticles. After loading, about 10–15 percent of the loaded polynucleotides will possess the unique restriction site distal from the microparticle surface. After digestion with the associated restriction endonuclease, an appropriate double stranded adaptor containing a biotin moiety is ligated to the sticky end. The resulting microparticles are then spread on the avidinated glass surface where they become fixed via the biotin-avidin linkages.

Alternatively and preferably when sequencing by ligation is employed, in the initial ligation step a mixture of probes is applied to the loaded microparticle: a fraction of the probes contain a type IIs restriction recognition site, as required by the sequencing method, and a fraction of the probes have no such recognition site, but instead contain a biotin moiety at its non-ligating end. Preferably, the mixture comprises about 10–15 percent of the biotinylated probe.

In still another alternative, when DNA-loaded microparticles are applied to a glass substrate, the DNA may non-specifically adsorb to the glass surface upon several hours, e.g. 24 hours, incubation to create a bond sufficiently strong to permit repeated exposures to reagents and washes without significant loss of microparticles. Preferably, such a glass substrate is a flow cell, which may comprise a channel etched in a glass slide. Preferably, such a channel is closed so that fluids may be pumped through it and has a depth sufficiently close to the diameter of the microparticles so that a monolayer of microparticles is trapped within a defined observation region.

Parallel Sequencing

The tagging system of the invention can be used with single base sequencing methods to sequence polynucleotides up to several kilobases in length. The tagging system permits many thousands of fragments of a target polynucleotide to be sorted onto one or more solid phase supports and sequenced simultaneously. In accordance with a preferred implementation of the method, a portion of each sorted fragment is sequenced in a stepwise fashion on each of the many thousands of loaded microparticles which are fixed to a common substrate-such as a microscope slide-associated with a scanning system or an image analysis system, such as described above. The size of the portion of the fragments sequenced depends of several factors, such as the number of fragments generated and sorted, the length of the target polynucleotide, the speed and accuracy of the single base method employed, the number of microparticles and/or discrete regions that may be monitored simultaneously; and the like. Preferably, from 12–50 bases are identified at each microparticle or region; and more preferably, 18–30 bases are identified at each microparticle or region. With this information, the sequence of the target polynucleotide is determined by collating the 12–50 base fragments via their overlapping regions, e.g. as described in U.S. Pat. No. 5,002,867. The following references provide additional guidance in determining the portion of the fragments that must be sequenced for successful reconstruction of a target polynucleotide of a given length: Lander and Waterman, Genomics, 2: 231–239 (1988); Drmanac et al, Genomics, 4: 114–128 (1989); Bains, DNA Sequencing and Mapping, 4: 143–150 (1993); Bains, Genomics, 11: 294–301 (1991); Drmanac et al, J. Biomolecular Structure and Dynamics, 8: 1085–1102 (1991); and Pevzner, J. Biomolecular Structure and Dynamics, 7: 63–73 (1989). Preferably, the length of the target polynucleotide is between 1 kilobase and 50 kilobases. More preferably, the length is between 10 kilobases and 40 kilobases. Lander and Waterman (cited above) provide guidance concerning the relationship among the number of fragments that are sequenced (i.e. the sample size), the amount of sequence information obtained from each fragment, and the probability that the target polynucleotide can be reconstructed from the partial sequences without gaps, or "islands." For the present invention, maximal polynucleotide sizes that can be obtained for given sample sizes and sizes of fragment sequences are shown below:

| | Approx. maximal target polynucleotide length | |
|---|---|---|
| Size of Sample | 30 bases/fragment | 50 bases/fragment |
| 1,000 | 3 kilobases | 4 kilobases |
| 10,000 | 22 kilobases | 32 kilobases |
| 20,000 | 40 kilobases | 65 kilobases |
| 30,000 | 60 kilobases | 85 kilobases |
| 100,000 | 180 kilobases | 300 kilobases |

Fragments may be generated from a target polynucleotide in a variety of ways, including so-called "directed" approaches where one attempts to generate sets of fragments covering the target polynucleotide with minimal overlap, and so-called "shotgun" approaches where randomly overlapping fragments are generated. Preferably, "shotgun" approaches to fragment generation are employed because of their simplicity and inherent redundancy. For example, randomly overlapping fragments that cover a target polynucleotide are generated in the following conventional "shotgun" sequencing protocol, e.g. as disclosed in Sambrook et al (cited above). As used herein, "cover" in this context means that every portion of the target polynucleotide sequence is represented in each size range, e.g. all fragments between 100 and 200 basepairs in length, of the generated fragments. Briefly, starting with a target polynucleotide as an insert in an appropriate cloning vector, e.g. phage, the vector is expanded, purified and digested with the appropriate restriction enzymes to yield about 10–15 jig of purified insert. Typically, the protocol results in about 500–1000 subclones per microgram of starting DNA. The insert is separated from the vector fragments by preparative gel electrophoresis, removed from the gel by conventional methods, and resuspended in a standard buffer, such as TE (Tris-EDTA). The restriction enzymes selected to excise the insert from the vector preferably leave compatible sticky ends on the insert, so that the insert can be self-ligated in preparation for generating randomly overlapping fragments. As explained in Sambrook et al (cited above), the circularized DNA yields a better random distribution of fragments than linear DNA in the fragmentation methods employed below. After self-ligating the insert, e.g. with T4 ligase using conventional protocols, the purified ligated insert is fragmented by a standard protocol, e.g. sonication or DNase I digestion in the presence of $Mn^{++}$. After fragmentation the ends of the fragments are repair, e.g. as described in Sambrook et al (cited above), and the repaired fragments are separated by size using gel electrophoresis. Fragments in the 300–500 basepair range are selected and eluted from the gel by conventional means, and ligated into a tag-carrying vector as described above to form a library of tag-fragment conjugates.

As described above, a sample containing several thousand tag-fragment conjugates are taken from the library and expanded, after which the tag-fragment inserts are excised from the vector and prepared for specific hybridization to the tag complements on microparticles, as described above. Depending of the size of the target polynucleotide, multiple samples may be taken from the tag-fragment library and separately expanded, loaded onto microparticles and sequenced. As discussed above, the number of doubles selected will depend on the fraction of the tag repertoire represented in a sample. (The probability of obtaining triples—three different polynucleotides with the same tag—or above can safely be ignored). As mentioned above, the probability of doubles in a sample can be estimated from the Poisson distribution $p(double)=m^2 e^{-m}/2$, where m is the fraction of the tag repertoire in the sample. Table VI below lists probabilities of obtaining doubles in a sample for given tag size, sample size, and repertoire diversity.

TABLE VIII

| Number of words in tag from 8 word set | Size of tag repertoire | Size of sample | Fraction of repertoire sampled | Probability of double |
|---|---|---|---|---|
| 7 | $2.1 \times 10^6$ | 3000 | $1.43 \times 10^{-3}$ | $10^{-6}$ |
| 8 | $1.68 \times 10^7$ | $3 \times 10^4$ | $1.78 \times 10^{-3}$ | $1.6 \times 10^{-6}$ |
| | | 3000 | $1.78 \times 10^{-4}$ | $1.6 \times 10^{-8}$ |
| 9 | $1.34 \times 10^8$ | $3 \times 10^5$ | $2.24 \times 10^{-3}$ | $2.5 \times 10^{-6}$ |
| | | $3 \times 10^4$ | $2.24 \times 10^{-4}$ | $2.5 \times 10^{-8}$ |

TABLE VIII-continued

| Number of words in tag from 8 word set | Size of tag repertoire | Size of sample | Fraction of repertoire sampled | Probability of double |
|---|---|---|---|---|
| 10 | $1.07 \times 10^9$ | $3 \times 10^6$ | $2.8 \times 10^{-3}$ | $3.9 \times 10^{-6}$ |
|  |  | $3 \times 10^5$ | $2.8 \times 10^{-4}$ | $3.9 \times 10^{-8}$ |

In any case, the loaded microparticles are then dispersed and fixed onto a glass microscope slide, preferably via an avidin-biotin coupling. Preferably, at least 15–20 nucleotides of each of the random fragments are simultaneously sequenced with a single base method. The sequence of the target polynucleotide is then reconstructed by collating the partial sequences of the random fragments by way of their overlapping portions, using algorithms similar to those used for assembling contigs, or as developed for sequencing by hybridization, disclosed in the above references.

Kits for Implementing the Method of the Invention

The invention includes kits for carrying out the various embodiments of the invention. Preferably, kits of the invention include a repertoire of tag complements attached to a solid phase support. Additionally, kits of the invention may include the corresponding repertoire of tags, e.g. as primers for amplifying the polynucleotides to be sorted or as elements of cloning vectors which can also be used to amplify the polynucleotides to be sorted. Preferably, the repertoire of tag complements are attached to microparticles. Kits may also contain appropriate buffers for enzymatic processing, detection chemistries, e.g. fluorescent or chemiluminescent tags, and the like, instructions for use, processing enzymes, such as ligases, polymerases, transferases, and so on. In an important embodiment for sequencing, kits may also include substrates, such as a avidinated microscope slides, for fixing loaded microparticles for processing.

Identification of Novel Polynucleotides in cDNA Libraries

Novel polynucleotides in a cDNA library can be identified by constructing a library of cDNA molecules attached to microparticles, as described above. A large fraction of the library, or even the entire library, can then be partially sequenced in parallel. After isolation of mRNA, and perhaps normalization of the population as taught by Soares et al, Proc. Natl. Acad. Sci., 91: 9228–9232 (1994), or like references, the following primer may by hybridized to the polyA tails for first strand synthesis with a reverse transcriptase using conventional protocols:

5'-mRNA-$[A]_n$-3'$[T]_{19}$-[primer (SEQ ID NO:9) site]-GG[W,W,W,C]$_9$ACCAGCTGATC-5' where [W,W,W,C]$_9$ represents a tag as described above, "ACCAGCTGATC" is an optional sequence (SEQ ID NO:10) forming a restriction site in double stranded form, and "primer site" is a sequence common to all members of the library that is later used as a primer binding site for amplifying polynucleotides of interest by PCR.

After reverse transcription and second strand synthesis by conventional techniques, the double stranded fragments are inserted into a cloning vector as described above and amplified. The amplified library is then sampled and the sample amplified. The cloning vectors from the amplified sample are isolated, and the tagged cDNA fragments excised and purified. After rendering the tag single stranded with a polymerase as described above, the fragments are methylated and sorted onto microparticles in accordance with the invention. Preferably, as described above, the cloning vector is constructed so that the tagged cDNAs can be excised with an endonuclease, such as Fok I, that will allow immediate sequencing by the preferred single base method after sorting and ligation to microparticles.

Stepwise sequencing is then carried out simultaneously on the whole library, or one or more large fractions of the library, in accordance with the invention until a sufficient number of nucleotides are identified on each cDNA for unique representation in the genome of the organism from which the library is derived. For example, if the library is derived from mammalian mRNA then a randomly selected sequence 14–15 nucleotides long is expected to have unique representation among the 2–3 thousand megabases of the typical mammalian genome. Of course identification of far fewer nucleotides would be sufficient for unique representation in a library derived from bacteria, or other lower organisms. Preferably, at least 20–30 nucleotides are identified to ensure unique representation and to permit construction of a suitable primer as described below. The tabulated sequences may then be compared to known sequences to identify unique cDNAs.

Unique cDNAs are then isolated by conventional techniques, e.g. constructing a probe from the PCR amplicon produced with primers directed to the prime site and the portion of the cDNA whose sequence was determined. The probe may then be used to identify the cDNA in a library using a conventional screening protocol.

The above method for identifying new cDNAs may also be used to fingerprint mRNA populations, either in isolated measurements or in the context of a dynamically changing population. Partial sequence information is obtained simultaneously from a large sample, e.g. ten to a hundred thousand, or more, of cDNAs attached to separate microparticles as described in the above method. The frequency distribution of partial sequences can identify mRNA populations from different cell or tissue types, as well as from diseased tissues, such as cancers. Such mRNA fingerprints are useful in monitoring and diagnosing disease states, e.g. International application PCT/US95/21944, which describes the use of express sequence tags (ESTs) for the same purpose.

Cycle Sequencing on Microparticles Loaded with Sorted Polynucleotides

Parallel sequencing may also be accomplished in accordance with the invention with conventional sequencing techniques that require the generation and separation of labeled DNA fragments. In particular, isolated microparticles loaded with a uniform population of templates may be used to generate labeled extension products by cycle sequencing. Cycle sequencing is a well-know variant of the basic Sanger approach to DNA sequencing describe fully in the following references: Craxton, Methods, Vol. 2 (February, 1991); Wozny, European patent publication 0 409 078 A2 (23 January 1991); Fuller, International application PCT/US92/07303; and Fuller, International application PCT/US94/03264. Briefly, in a standard sequencing reaction mixture, a thermal stable polymerase is employed so that repeated extension reactions may be carried out on the same template. This permits small amounts of template to generate sufficient amounts of extension product for detection after separation by electrophoresis. Typically, cycle sequencing comprises the steps of (a) providing a sequencing reaction mixture with a template, a primer, nucleoside triphosphates, chain-terminating nucleoside triphosphates, and a thermal stable DNA polymerase; (b) denaturing the template, (c) annealing the primer to the denatured template, (d) extending the primer to form extension products, and (e) repeating steps (b)–(d) until sufficient quantities of extension products are accumulated so that they may be detected upon separation. The number of times the cycle is repeated depends on many factors, including the amount and quality of starting template, the detection system employed, the separation system employed, and the like. As conventionally practiced, the extension cycle is typically repeated from 10 to 100 times; the template amount ranges from as little as a few tens of femtomole to several tens of picomole; the denaturation step is carried out by heating the reaction mixture to a temperature in the range of 92–95° C.; the annealing step takes place at a temperature in the range of 35–75° C.; and the extension step takes place at a temperature in the range of 65–85° C. with a thermal stable DNA polymerase, such as Taq or Vent (available from Perkin-Elmer Corp., Norwalk, Conn., and New England Biolabs, respectively).

Tag complements may be prepared on magnetic microparticles as described by Albretsen et al, Anal. Biochem., 189: 40–50 (1990), which allows loadings of several femtomoles of tag complements onto 4.5 jum diameter magnetic beads. Tag complements may be attached to the microparticles either by their 5' or 3' ends. If attached by 5' ends, then the templates may be sorted via specific hybridization of tags at their 3' ends. In this embodiment, the template has a primer complement at its 5' end, as shown below:

3'-[oligonucleotide tag]-[template]-[primer complement]-5'

The tag complement is then extended the length of the template so that a complement of the template is obtained which is covalently attached to the microparticle. The template is removed by heating and the microparticles are washed. After microparticles are separated, e.g. by flow sorting, repeated cycles of annealing primers, extension, and denaturation are carried out.

If tag complements are attached to the microparticles by their 3' ends, which allows for convenient synthesis directly on the microparticles, the order of the oligonucleotide tag and primer complement are reversed, as shown below:

5'-[oligonucleotide tag]-[template]-[primer complement]-3'

Also, the 5' end of the tag complement is phosphorylated, e.g. using commercially available reagents. After specific hybridization via the oligonucleotide tag, a primer is annealed to the primer complement at the 3' end of the template and extended with a DNA polymerase lacking 3'→5' exonuclease activity. The nick left by this extension reaction is then ligated and the original template removed by heating. After separating microparticles, the cycle sequencing can be carried out as above.

Separation of loaded microparticles may be carried out by flow sorting, wherein suspended microparticles are entrained to pass single file through a nozzle and in a liquid jet which is broken up into a regular series of charged droplets which are directed to predetermined target vessels, wells, or other reaction locations on a substrate. Microparticles are conveniently detected in the jet by light scatter and the magnitude of the scatter is used to determine whether a droplet contains no, one, or multiple microparticles. A particularly useful apparatus for such flow sorting and delivery of sequencing reagent is disclosed in Brennan, International application PCT/US94/05896. Once the individual loaded microparticles are distributed to a plurality of reaction sites or wells with the appropriate sequencing reagents, the collection of reactions can be thermally cycled together to generate extension products. After cycling is completed, the extension products are separated by electrophoresis. Preferably, electrophoretic separation is carried out by capillary electrophoresis in a gel-free separation medium, which allows convenient loading and rapid separation of the extension fragments. Also, apparatus is available which permits detection by four-color fluorescence of a large number of samples substantially at the same time, e.g. the type disclosed by Mathies and Huang, Nature, 359:167–169 (1992); Huang et al, Anal. Chem., 64: 2149–2154 (1992); Huang et al, Anal. Chem., 64: 967–972 (1992); or the like. Preferably, several thousand cycle sequencing reactions are carried at the same time. More preferably, mixtures of templates are sorted onto a population of microparticles having a repertoire of oligonucleotide tags of between 1000 and 10,000 different types.

Sorting Multi-locus Probes for Genotypic Analysis

Many disease conditions and/or disease susceptibilities are associated with complex genetic traits and/or patterns of mutation, e.g. HLA type, mutation pattern of the p53 gene in many cancers, the cystic fibrosis gene, Lesch-Nyhan syndrome, Duchenne muscular dystrophy, and the like, Lander et al, Science, 265: 2037–2048 (1994); Collins, Science, 256:774–779 (1992); Tsui et al, International patent application PCT/CA90/00267; Hedrum et al, Biotechniques, 17: 118–129 (1994); Santamaria et al, International patent application PCT/US92/01675; Chamberlain et al, Nucleic Acids Research, 16: 11141–11156 (1988); and the like. One approach to constructing convenient assays for such complex genetic traits has been to use so-called multiplex PCR or multiplex ligation assays, such as described in Chamberlain et al (cited above) or in Grossman et al, International patent application PCT/US93/03229. Usually, such techniques call for the simultaneous amplification of multiple genetic sequences in the same reaction mixture followed by specific detection of sequences of interest. Oligonucleotide tags of the invention can provide a simple and convenient means for identifying genetic sequences that are amplified in such assays. In its simplest form, this embodiment of the invention may be implement by attaching oligonucleotide tags to PCR primers used in multiplex PCR One primer of a pair carries an oligonucleotide tag and the other primer of the pair carries a capture moiety, such as described above, that permits isolation and then release of successfully amplified sequences. After release, the sequences are applied to solid phase support having a set of tag complements attached at predefined spatial addresses. The pattern of specific hybridization of the tags is then detected to identify the genotype of a sample.

In a preferred embodiment, PCR is employed to amplify a genetic sequences of interest that contains multiple target sites, i.e. multiple sites where mutations or disease-related sequences occur. Preferably, only two or very few pairs of primers are used to amplify the target sequence to avoid the difficulties involved with multiplex PCR, such as balancing target lengths, primer annealing temperatures, and the like. After amplification, specific genotypes are detected in a manner analogous to that described in Grossman et al (cited above) and Grossman et al, U.S. Pat. No. 5,514,543, which references provide guidance in the selection of PCR and ligation reaction conditions, ligation probe sizes, and the like. In those references, a target sequence is similarly amplified, after which a collection of ligation probes are applied in the presence of a DNA ligase. The ligation probes consist of two separate sequences both complementary to a target potentially present in a sample being analyzed: one is attached to a electrophoretic mobility modifier and the other is attached to a fluorescent label. If the two probes form perfect duplexes with the target sequence in the sample they are ligated so that the mobility modifying moiety is now attached to a fluorescent label through the ligated sequences complementary to the target. The components of the mixture are then separated electrophoretically so that the pattern of fluorescent bands on a gel is indicative of the genotype of the target present in the sample. As shown in FIG. 3, oligonucleotide tags of the invention may be used in place of the electrophoretic mobility modifiers and spatial separation can be achieved by sorting ligated sequences to particular locations on a solid phase support. Returning to FIG. 3, target sequence (200) is amplified, preferably by PCR, after which a collection of ligation probes (206–216) is applied (204) to a denatured amplicon. In this embodiment, ligation probes comprise an oligonucleotide tag (206), a first sequence (208) complementary to a target sequence, a second sequence (210) complementary to the target sequence and contiguous with the first sequence (such that if both are perfectly complementary to the target sequence they are capable of being ligated), a tail (212) carrying a signal generating means (214). Signal generating means (214) is preferably a fluorescent label. Preferably, the first and second sequences of the ligation probes are ligated by a DNA ligase; thus, the 5' end of the abutting sequences (216) must be phosphorylated, e.g. via a phosphorylating reagent described in Urdea et al, U.S. Pat. No. 5,332,845. After application of the ligation probes and a ligase, probes forming perfectly matched duplexes with the target sequence are covalently joined (218 & 220). The probe-target duplexes are then denatured and applied (222) to a solid phase support which has tag complements attached at well defined spatial locations for every tag $t_l$ through $t_k$. After washing off nonspecifically bound sequences, the spatial locations corresponding to the tag complements of the oligonucleotide tags, $t_i$ and $t_j$, which were ligated to fluorescent labels are illuminated, as shown in FIG. 3 by 226 and 228. The pattern of illuminated fluorophors on the solid phase support indicates the genotype of the target sequence in the sample. Preferably, in this embodiment of the invention there is a one-to-one correspondence between a tag and a spatial address on the solid phase support. In further preference, this embodiment is employed to simultaneously identify at least twenty gene targets; and more preferably, it is employed to simultaneously detect at least 50 gene targets.

Generally, this embodiment of the invention may be with the following steps for detecting the presence or absence of a plurality of selected target sequences in a target polynucleotide: (1) adding to the target polynucleotide a plurality of ligation probes, each ligation probe including a first oligonucleotide and a second oligonucleotide which are complementary in sequence to adjacent portions of a selected one of the target sequences in the target polynucleotide, the first oligonucleotide having an oligonucleotide tag attached, each oligonucleotide tag being selected from the same minimally cross-hybridizing set and each ligation probe having a different oligonucletide tag; (2) hybridizing the probes with the target polynucleotide; (3) treating the hybridized first and second oligonucleotides under conditions effective to ligate the first and second oligonucleotides whenever the first and second oligos form perfectly match duplexes with adjacent target sequences; (4) separating ligated first and second oligos from unligated first and second oligonucleotides; (5) sorting the ligated first and second oligonucleotides by specifically hybridizing the oligonucleotide tags with their respective complements, the respective complements being attached as uniform populations of substantially identical oligonucleotides in spatially discrete regions on the one or more solid phase supports; and (6) detecting the presence or absence of the selected target sequences by the presence or absence of ligated first and second oligonucleotides on the one or more solid phase supports.

EXAMPLE 1

Sorting Multiple Target Polynucleotides Derived from pUC19

A mixture of three target polynucleotide-tag conjugates are obtained as follows: First, the following six oligonucleotides are synthesized and combined pairwise to form tag 1, tag 2, and tag 3 (SEQ ID NO:11, SEQ ID NO:12, and SEQ ID NO:13):

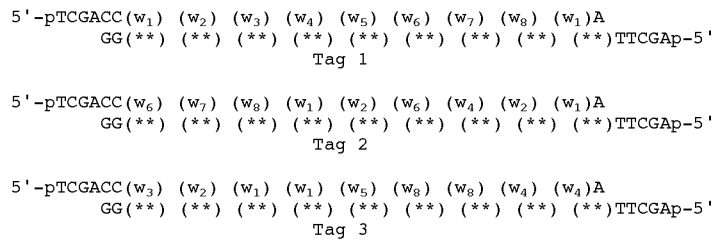

where "p" indicates a monophosphate, the $w_i$'s represent the subunits define in Table II, and the terms "(**)" represent their respective complements. A pUC 19 is digested with Sal I and Hind III, the large fragment is purified, and separately ligated with tags 1, 2, and 3, to form pUC19-1, pUC19-2, and pUC19-3, respectively. The three recombinants are separately amplified and isolated, after which pUC19-1 is digested with Hind III and Aat I, pUC19-2 is digested with Hind III and Ssp I, and pUC19-3 is digested with Hind III and Xmn I. The small fragments are isolated using conventional protocols to give three double stranded fragments about 250, 375, and 575 basepairs in length, respectively, and each having a recessed 3' strand adjacent to the tag and a blunt or 3' protruding strand at the opposite end. Approximately 12 nmoles of each fragment are mixed with 5 units T4 DNA polymerase in the manufacturer's recommended reaction buffer containing 33 M deoxycytosine triphosphate. The reaction mixture is allowed to incubate at 37° C. for 30 minutes, after which the reaction is stopped by placing on ice. The fragments are then purified by conventional means.

CPG microparticles (37–74 mm particle size, 500 angstrom pore size, Pierce Chemical) are derivatized with the linker disclosed by Maskos and Southern, Nucleic Acids Research, 20: 1679–1684 (1992). After separating into three aliquots, the complements of tags 1, 2, and 3 are synthesized on the microparticles using a conventional automated DNA synthesizer, e.g. a model 392 DNA synthesizer (Applied Biosystems, Foster City, CA). Approximately 1 mg of each of the differently derivatized microparticles are placed in separate vessels.

The T4 DNA polymerase-treated fragments excised from pUC19-1, -2, and -3 are resuspended in 50 L of the manufacturer's recommended buffer for Taq DNA ligase (New England Biolabs). The mixture is then equally divided among the three vessels containing the 1 mg each of derivatized CPG microparticles. 5 units of Taq DNA ligase is added to each vessel, after which they are incubated at 55° C. for 15 minutes. The reaction is stopped by placing on ice and the microparticles are washed several times by repeated centrifugation and resuspension in TE. Finally, the microparticles are resuspended in Nde I reaction buffer (New England Biolabs) where the attached polynucleotides are digested. After separation from the microparticles the polynucleotide fragments released by Nde I digestion are fluorescently labeled by incubating with Sequenase DNA polymerase and fluorescein labeled thymidine triphosphate (Applied Biosystems, Foster City, Calif.). The fragments are then separately analyzed on a nondenaturing polyacrylamide gel using an Applied Biosystems model 373 DNA sequencer.

EXAMPLE 2

Parallel Sequencing of SV40 Fragments

A repertoire of 36-mer tags consisting of nine 4-nucleotide subunits selected from Table II is prepared by separately synthesizing tags and tag complements by a split and mix approach, as described above. The repertoire is synthesized so as to permit ligation into a Sma I/Hind III digested M13mp19. Thus, as in Example 1, one set of oligonucleotides begins with the addition of A followed by nine rounds of split and mix synthesis wherein the oligonucleotide is extended subunit-wise by 3'-phosphoramidite derivatived 4-mers corresponding to the subunits of Table II. The synthesis is then completed with the nucleotide-by-nucleotide addition of one half of the Sma I recognition site (GGG), two C's, and a 5'-monophosphate, e.g. via the Phosphate-ON reagent available from Clontech Laboratories (Palo Alto, Calif.). The other set of oligonucleotides begins with the addition of three C's (portion of the Sma I recognition site) and two G's, followed by nine rounds of split and mix synthesis wherein the oligonucleotide is extended by 3'-phosphoramidite derivatized 4-mers corresponding to the complements of the subunits of Table II. Synthesis is completed by the nucleotide-by-nucleotide addition of the Hind III recognition site and a 5'-monophosphate. After separation from the synthesis supports the oligonucleotides are mixed under conditions that permit formation of the following duplexes (SEQ ID NO:14):

Next the following adaptor (SEQ ID NO:15) is prepared which contains a Fok I site and portions of Eco RI and Sma I sites:

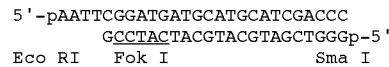
```
5'-pAATTCGGATGATGCATGCATCGACCC
        GCCTACTACGTACGTAGCTGGGp-5'
Eco RI   Fok I              Sma I
```

The adaptor is ligated into the Eco RI/Sma I digested M13 described above.

Separately, SV40 DNA is fragmented by sonication following the protocol set forth in Sambrook et al (cited above). The resulting fragments are repaired using standard protocols and separated by size. Fragments in the range of 300–500 basepairs are selected and ligated into the Sma I digested M13 described above to form a library of fragment-tag conjugates, which is then amplified. A sample containing several thousand different fragment-tag conjugates is taken from the library, further amplified, and the fragment-tag inserts are excised by digesting with Eco RI and Hind III. The excised fragment-tag conjugates are treated with T4 DNA polymerase in the presence of deoxycytidine triphosphate, as described in Example I, to expose the oligonucleotide tags for specific hybridization to the CPG microparticles.

After hybridization and ligation, as described in Example 1, the loaded microparticles are treated with Fok I to produce a 4-nucleotide protruding strand of a predetermined sequence. A 10:1 mixture (probe 1:probe 2) of the following probes (SEQ ID NO:16 and SEQ ID NO:17) are ligated to the polynucleotides on microparticles.

Probe 1 FAM-ATCGGATGAC TAGCCTACTGAGCT
Probe 2 biotin-ATCCAATGAC TAGGTTACTGAGCT

FAM represents a fluorescein dye attached to the 5'-hydroxyl of the top strand of Probe 1 through an aminophosphate linker available from Applied Biosystems (Aminolinker). The biotin may also be attached through an Aminolinker moiety and optionally may be further extended via polyethylene oxide linkers, e.g. Jaschke et al (cited above).

The loaded microparticles are then deposited on the surface of an avidinated glass slide to which and from which reagents and wash solutions can be delivered and removed. The avidinated slide with the attached microparticles is examined with a scanning fluorescent microscope (e.g. Zeiss Axioskop equipped with a Newport Model PM500-C motion controller, a Spectra-Physics Model 2020 argon ion laser producing a 488 nm excitation beam, and a 520 nm long-pass emission filter, or like apparatus). The excitation beam and fluorescent emissions are delivered and collected, respectively, through the same objective lens. The excitation beam and collected fluorescence are separated by a dichroic mirror which directs the collected fluorescence through a series of bandpass filters and to photon-counting devices corresponding to the fluorophors being monitored, e.g. comprising Hamamatsu model 9403–02 photomultipliers, a Stanford Research Systems model SR445 amplifier and model SR430 multichannel scaler, and digital computer, e.g. a 486-based computer. The computer generates a two dimensional map of the slide which registers the positions of the microparticles.

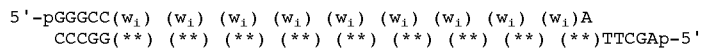
```
5'-pGGGCC(w_i) (w_i) (w_i) (w_i) (w_i) (w_i) (w_i) (w_i) (w_i)A
   CCCGG(**)  (**)  (**)  (**)  (**)  (**)  (**)  (**)  (**)TTCGAp-5'
```

The mixture of duplexes is then ligated into a Sma I/Hind HII-digested M13mp19. A repertoire of tag complements are synthesized on CPG microparticles as described above.

After cleavage with Fok I to remove the initial probe, the polynucleotides on the attached microparticles undergo 20 cycles of probe ligation, washing, detection, cleavage, and washing, in accordance with the preferred single base sequencing methodology described below. Within each detection step, the scanning system records the fluorescent emission corresponding the base identified at each microparticle. Reactions and washes below are generally carried out with manufacturer's (New England Biolabs') recommended buffers for the enzymes employed, unless otherwise indicated. Standard buffers are also described in Sambrook et al (cited above).

The following four sets of mixed probes are provided for addition to the target polynucleotides:

TAMRA-ATCGGATGACATCAAC TAGCCTACTG- TAGTTGANNN

FAM-ATCGGATGACATCAAC TAGCCTACTGTAGT- TGCNNN

ROX-ATCGGATGACATCAAC TAGCCTACTGTAGT- TGGNNN

JOE-ATCGGATGACATCAAC TAGCCTACTGTAGT- TGTNNN where TAMRA, FAM, ROX, and JOE are spectrally resolvable fluorescent labels attached by way of Aminolinker II (all being available from Applied Biosystems, Inc., Foster City, Calif.); the bold faced nucleotides are the recognition site for Fok I endonuclease, and "N" represents any one of the four nucleotides, A, C, G, T. TAMRA (tetramethylrhodamine), FAM (fluorescein), ROX (rhodamine X), and JOE (2',7'-iethoxy4',5'-dichlorofluorescein) and their attachment to oligonucleotides is also described in Fung et al, U.S. Pat. No. 4,855,225.

The above probes are incubated in approximately 5 molar excess of the target polynucleotide ends as follows: the probes are incubated for 60 minutes at 16° C. with 200 units of T4 DNA ligase and the anchored target polynucleotide in T4 DNA ligase buffer, after washing, the target polynucleotide is then incubated with 100 units T4 polynucleotide kinase in the manufacturer's recommended buffer for 30 minutes at 37° C., washed, and again incubated for 30 minutes at 16° C. with 200 units of T4 DNA ligase and the anchored target polynucleotide in T4 DNA ligase buffer. Washing is accomplished by successively flowing volumes of wash buffer over the slide, e.g. TE, disclosed in Sambrook et al (cited above). After the cycle of ligation-phosphorylation-ligation and a final washing, the attached microparticles are scanned for the presence of fluorescent label, the positions and characteristics of which are recorded by the scanning system. The labeled target polynucleotide, i.e. the ligated complex, is then incubated with 10 units of Fok I in the manufacturer's recommended buffer for 30 minutes at 37° C., followed by washing in TE. As a result the target polynucleotide is shortened by one nucleotide on each strand and is ready for the next cycle of ligation and cleavage. The process is continued until twenty nucleotides are identified.

EXAMPLE 3

Construction of a Tag Library

An exemplary tag library is constructed as follows to form the chemically synthesized 9-word tags (SEQ ID NO:22) of nucleotides A, G, and T defined by the formula:

3'-TGGC-[$^4$(A,G,T)$_9$]-CCCCp where "[$^4$((A,G,T)$_9$]" indicates a tag mixture where each tag consists of nine 4-mer words of A, G, and T; and "p" indicate a 5' phosphate. This mixture is ligated to the following right and left primer binding regions (SEQ ID NO:23 and SEQ ID NO:24):

```
5'- AGTGGCTGGGCATCGGACCG   5'- GGGGCCCAGTCAGCGTCGAT
    TCACCGACCCGTAGCCp          GGGTCAGTCGCAGCTA
         LEFT                        RIGHT
```

The right and left primer binding regions are ligated to the above tag mixture (SEQ ID NO:22); after which the single stranded portion of the ligated structure is filled with DNA polymerase then mixed with the right and left primers indicated below (SEQ ID NO:25 and SEQ ID NO:26) and amplified to give a tag library.

```
            Left Primer
       5'- AGTGGCTGGGCATCGGACCG

5'- AGTGGCTGGGCATCGGACCG- 4(A,G,T)9-GGGGCCCAGTCAGCGTCGAT
           TCACCGACCCGTAGCCTGGC- 4(A,G,T)9-CCCCGGGTCAGTCGCAGCTA

CCCCGGGTCAGTCGCAGCTA-
       5'
                                                    Right Primer
```

The underlined portion of the left primer binding region indicates a Rsr II recognition site. The left-most underlined region of the right primer binding region indicates recognition sites for Bsp 120I, Apa I, and Eco O 109I, and a cleavage site for Hga I. The right-most underlined region of the right primer binding region indicates the recognition site for Hga I. Optionally, the right or left primers may be synthesized with a biotin attached (using conventional reagents, e.g. available from Clontech Laboratories, Palo Alto, Calif.) to facilitate purification after amplification and/or cleavage.

EXAMPLE 4

Construction of a Plasmid Library of Tag- Polynucleotide Conjugates for cDNA "Signature" Sequencing cDNA is produced from an mRNA sample by conventional protocols using pGGCCCT$_{15}$(A or G or C) as a primer for first strand synthesis anchored at the boundary of the poly A region of the mRNAs and N$_8$(A or T)GATC as the primer for second strand synthesis. That is, both are degenerate primers such that the second strand primer is present in two forms and the first strand primer is present in three forms. The GATC sequence in the second strand primer corresponds to the recognition site of Mbo I; other four base recognition sites could be used as well, such as those for Bam HI, Sph I, Eco RI, or the like. The presence of the A and T adjacent to the restriction site of the second strand primer ensures that a stripping and exchange reaction can be used in the next step to generate a five-base 5' overhang of "GGCCC". The first strand primer is annealed to the mRNA sample and extended with reverse transcriptase, after which the RNA strand is degraded by the RNase H activity of the reverse transcriptase leaving a single stranded cDNA. The second strand primer is annealed and extended with a DNA polymerase using conventional protocols. After second strand synthesis, the resulting cDNAs are methylated with CpG methylase (New England Biolabs, Beverly, Mass.) using manufacturer's protocols. The 3' strands of the cDNAs are then cut back with the above-mentioned stripping and exchange reaction using T4 DNA polymerase in the presence of DATP and dTIP, after which the cDNAs are ligated to the tag library of Example 3 previously cleaved with Hga I to give the following construct:

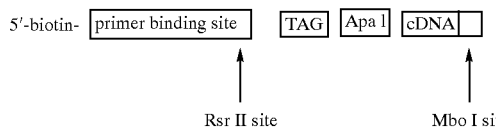

Separately, the following cloning vector (SEQ ID NO:27) is constructed, e.g. starting from a commercially available plasmid, such as a Bluescript phagemid (Stratagene, La Jolla, Calif.).

```
              primer binding site
                       ↓
(plasmid)-5' -AAAAGGAGGAGGCCTTGATAGAGAGGACCT-
             -TTTTCCTCCTCCGGAACTATCTCTCCTGGA- Ppu MI site     primer binding site
            ↓                    ↓
       -GTTTAAAC-GGATCC-TCTTCCTCTTCCTCTTCC-3'-(plasmid)
       -CAAATTTG-CCTAGG-AGAAGGAGAAGGAGAAGG-
            ↑        ↑
                  BamHI site
        Pme I site
```

The plasmid is cleaved with Ppu MI and Pme I (to give a Rsr II-compatible end and a flush end so that the insert is oriented) and then methylated with DAM methylase. The tag-containing construct is cleaved with Rsr II and then ligated to the open plasmid, after which the conjugate is cleaved with Mbo I and Bam HI to permit ligation and closing of the plasmid. The plasmid is then amplified and isolated and used in accordance with the invention.

APPENDIX Ia

Exemplary computer program for generating minimally cross hybridizing sets
(single stranded tag/single stranded tag complement)

```
Program minxh
c
c
c
         integer*2 sub1(6),mset1(1000,6),mset2(1000,6)
         dimension nbase(6)
c
c
         write(*,*)'ENTER SUBUNIT LENGTH'
         read(*,100)nsub
100     format(i1)
         open(1,file='sub4.dat',form='formatted',status='new')
c
c
         nset=0
         do 7000 m1=1,3
            do 7000 m2=1,3
               do 7000 m3=1,3
                  do 7000 m4=1,3
```

APPENDIX Ia-continued

Exemplary computer program for generating minimally cross hybridizing sets
(single stranded tag/single stranded tag complement)

```
                     sub1(1)=m1
                     sub1(2)=m2
                     sub1(3)=m3
                     sub1(4)=m4
c
c
         ndiff=3
c
c
c
c               Generate set of subunits differing from
c               sub1 by at least ndiff nucleotides.
c               Save in mset1.
c
         jj=1
         do 900 j=1,nsub
900          mset1(1,j)=sub1(j)
c
c
```

APPENDIX Ia-continued

Exemplary computer program for generating minimally cross hybridizing sets
(single stranded tag/single stranded tag complement)

```
         do 1000 k1=1,3
            do 1000 k2=1,3
               do 1000 k3=1,3
                  do 1000 k4=1,3
c
c
                     nbase(1)=k1
                     nbase(2)=k2
                     nbase(3)=k3
                     nbase(4)=k4
c
                     n=0
                     do 1200 j=1,nsub
                        if(sub1(j).eq.1 .and. nbase(j).ne.1 .or.
1                          sub1(j).eq.2 .and. nbase(j).ne.2 .or.
3                          sub1(j).eq.3 .and. nbase(j) .ne.3) then
                            n=n+1
                        endif
1200                 continue
c
c
                     if(n.ge.ndiff) then
c
c
c
c                           If number of mismatches
c                           is greater than or equal
c                           to ndiff then record
c                           subunit in matrix mset
```

APPENDIX Ia-continued

Exemplary computer program for generating
minimally cross hybridizing sets
(single stranded tag/single stranded tag complement)

```
c
                jj=jj+1
                do 1100 i=1,nsub
1100                mset1(jj,i)=nbase(i)
            endif
c
c
1000    continue
c
c
            do 1325 j2=1,nsub
            mset2(1,j2)=mset1(1,j2)
1325        mset2(2,j2)=mset1(2,j2)
c
c
c                                   Compare subunit 2 from
c                                   mset1 with each successive
c                                   subunit in mset1, i.e. 3,
c                                   4,5, . . . etc. Save those
c                                   with mismatches .ge. ndiff
c                                   in matrix mset2 starting at
c                                   position 2.
c                                       Next transfer contents
c                                   of mset2 into mset1 and
c                                   start
c                                   comparisons again this time
c                                   starting with subunit 3.
c                                   Continue until all subunits
c                                   undergo the comparisons.
c
            npass=0
c
c
1700    continue
            kk=npass+2
            npass=npass+1
c
c
            do 1500 m=npass+2,jj
                n=0
                do 1600 j=1,nsub
                    if(mset1(npass+1,j).eq.1.and.mset1(m,j).ne.1.or.
     2              mset1(npass+1,j).eq.2.and.mset1(m,j).ne.2.or.
     2              mset1(npass+1,j).eq.3.and.mset1(m,j).ne.3) then
                    n=n+1
                    endif
1600            continue
                if(n.ge.ndiff) then
                    kk=kk+1
                    do 1625 i=1,nsub
1625                    mset2(kk,i)=mset1(m,i)
                endif
1500        continue
c
c                                   kk is the number of subunits
c                                   stored in mset2
c
c                                   Transfer contents of mset2
c                                   into mset1 for next pass.
c
            do 2000 k=1,kk
                do 2000 m=1,nsub
2000                mset1(k,m)=mset2(k,m)
            if(kk.lt.jj) then
                jj=kk
                goto 1700
            endif
c
c
            nset=nset+1
            write(1,7009)
7009        format(/)
            do 7008 k=1,kk
```

APPENDIX Ia-continued

Exemplary computer program for generating
minimally cross hybridizing sets
(single stranded tag/single stranded tag complement)

```
7008            write(1,7010)(mset1(k,m),m=1,nsub)
7010        format(4i1)
            write(*,*)
            write(*,120) kk,nset
120         format(1x,'Subunits in set=',i5,2x,'Set No=',i5)
7000    continue
        close(1)
c
c
        end
c                               *********************************
c                               *********************************
```

APPENDIX Ib

Exemplary computer program for generating
minimally cross hybridizing sets
(single stranded tag/single stranded tag complement)

```
Program tagN
c
c           Program tagN generates minimally cross-hybridizing
c           sets of subunits given i) N--subunit length, and ii)
c           an initial subunit sequence. tagN assumes that only
c           3 of the four natural nucleotides are used in the tags.
c
        character*1 sub1(20)
        integer*2 mset(10000,20), nbase(20)
c
c
        write(*,*)'ENTER SUBUNIT LENGTH'
        read(*,100)nsub
100     format(i2)
c
        write(*,*)'ENTER SUBUNIT SEQUENCE'
        read(*,110)(sub1(k),k=1,nsub)
110     format(20a1)
c
        ndiff=10
c
c           Let a=1 c=2 g=3 & t=4
c
        do 800 kk=1,nsub
            if(sub1(kk).eq.'a') then
                mset(1,kk)=1
            endif
                if(sub1(kk).eq.'c') then
                    mset(1,kk)=2
                endif
                    if(sub1(kk).eq.'g') then
                        mset(1,kk)=3
                    endif
                        if(sub1(kk).eq.'t') then
                            mset(1,kk)=4
                        endif
800     continue
c
c
c           Generate set of subunits differing from
c           sub1 by at least ndiff nucleotides.
c
        jj=1
c
        do 1000 k1=1,3
```

APPENDIX Ib-continued

Exemplary computer program for generating
minimally cross hybridizing sets
(single stranded tag/single stranded tag complement)

```
                        do 1000 k2=1,3
                          do 1000 k3=1,3
                            do 1000 k4=1,3
                              do 1000 k5=1,3
                                do 1000 k6=1,3
                                  do 1000 k7=1,3
                                    do 1000 k8=1,3
                                      do 1000 k9=1,3
                                        do 1000 k10=1,3
            do 1000 k11=1,3
              do 1000 k12=1,3
                do 1000 k13=1,3
                  do 1000 k14=1,3
                    do 1000 k15=1,3
                      do 1000 k16=1,3
                        do 1000 k17=1,3
                          do 1000 k18=1,3
                            do 1000 k19=1,3
                              do 1000 k20=1,3
c
c
                        nbase(1)=k1
                        nbase(2)=k2
                        nbase(3)=k3
                        nbase(4)=k4
                        nbase(5)=k5
                        nbase(6)=k6
                        nbase(7)=k7
                        nbase(8)=k8
                        nbase(9)=k9
                        nbase(10)=k10
                        nbase(11)=k11
                        nbase(12)=k12
                        nbase(13)=k13
                        nbase(14)=k14
                        nbase(15)=k15
                        nbase(16)=k16
                        nbase(17)=k17
                        nbase(18)=k18
                        nbase(19)=k19
                        nbase(20)=k20
c
c
                  do 1250 nn=1,jj
c
                    n=0
                    do 1200 j=1,nsub
                      if(mset(nn,j).eq.1 .and. nbase(j).ne.1 .or.
     1                   mset(nn,j).eq.2 .and. nbase(j).ne.2 .or.
     2                   mset(nn,j).eq.3 .and. nbase(j).ne.3 .or.
     3                   mset(nn,j).eq.4 .and. nbase(j).ne.4) then
                        n=n+1
                      endif
1200                continue
c
c
                  if(n.lt.ndiff) then
                    goto 1000
                  endif
1250              continue
c
c
                  jj=jj+1
                  write(*,130)(nbase(1),i=1,nsub),jj
                  do 1100 i=1,nsub
                    mset(jj,i)=nbase(1)
1100              continue
c
c
1000   continue
c
c
      write(*,*)
130   format(10x,20(1x,i1),5x,i5)
      write(*,*)
      write(*,120) jj
120   format(1x,'Number of words=',i5)
c
c
      end
c
c   **********************************************
c   **********************************************
```

APPENDIX Ic

Exemplary computer program for generating
minimally cross hybridizing sets
(double stranded tag/single stranded tag complement)

```
Program 3tagN
c
c       Program 3tagN generates minimally cross-hybridizing
c           sets of duplex subunits given i) N--subunit length,
c           and ii) an initial homopurine sequence.
c
      character*1 sub1(20)
      integer*2 mset(10000,20), nbase(20)
c
      write(*,*)'ENTER SUBUNIT LENGTH'
      read(*,100)nsub
100   format(12)
c
      write(*,*)'ENTER SUBUNIT SEQUENCE a & g only'
      read(*,110) (sub1(k),k=1,nsub)
110   format(20a1)
c
      ndiff=10
c
c           Let a=1 and g=2
c
      do 800 kk=1,nsub
        if(sub1(kk).eq.'a') then
          mset(1,kk)=1
        endif
        if(sub1(kk).eq.'g') then
          mset(1,kk)=2
        endif
800   continue
c
      jj=1
c
      do 1000 k1=1,3
        do 1000 k2=1,3
          do 1000 k3=1,3
            do 1000 k4=1,3
              do 1000 k5=1,3
                do 1000 k6=1,3
                  do 1000 k7=1,3
                    do 1000 k8=1,3
                      do 1000 k9=1,3
                        do 1000 k10=1,3
            do 1000 k11=1,3
              do 1000 k12=1,3
                do 1000 k13=1,3
                  do 1000 k14=1,3
                    do 1000 k15=1,3
                      do 1000 k16=1,3
                        do 1000 k17=1,3
                          do 1000 k18=1,3
                            do 1000 k19=1,3
                              do 1000 k20=1,3
                        nbase(1)=k1
                        nbase(2)=k2
                        nbase(3)=k3
                        nbase(4)=k4
                        nbase(5)=k5
```

APPENDIX Ic-continued

Exemplary computer program for generating
minimally cross hybridizing sets
(double stranded tag/single stranded tag complement)

```
              nbase(6)=k6
              nbase(7)=k7
              nbase(8)=k8
              nbase(9)=k9
              nbase(10)=k10
              nbase(11)=k11
              nbase(12)=k12
              nbase(13)=k13
              nbase(14)=k14
              nbase(15)=k15
              nbase(16)=k16
              nbase(17)=k17
              nbase(18)=k18
              nbase(19)=k19
              nbase(20)=k20
c
              do 1250 nn=1,jj
c
              n=0
              do 1200 j=1,nsub
                 if(mset(nn,j).eq.1 .and. nbase(j).ne.1 .or.
     1              mset(nn,j).eq.2 .and. nbase(j).ne.2 .or.
     2              mset(nn,j).eq.3 .and. nbase(j).ne.3 .or.
     3              mset(nn,j).eq.4 .and. nbase(j).ne.4) then
                    n=n+1
                 endif
1200          continue
c
              if (n.lt.ndiff) then
                 goto 1000
              endif
1250       continue
c
              jj=jj+1
              write(*,130)(nbase(1),i=1,nsub),jj
              do 1100 i=1,nsub
                 mset(jj,i)=nbase(1)
1100          continue
1000       continue
c
           write(*,*)
130        format(10x,20(1x,i1),5x,i5)
           write(*,*)
           write(*,120) jj
120        format(1x,'Number of words=',i5)
c
c
           end
```

I claim:

1. A repertoire of oligonucleotide tags, the repertoire comprising oligonucleotides selected from the group consisting of oligonucleotides of the formula:

$S_1S_2S_3 \ldots S_n$ wherein each of $S_1$ through $S_n$ are subunits consisting of an oligonucleotide having a length from three to nine nucleotides and being selected from a minimally cross-hybridizing set;

n is in the range of from 4 to 10, with the proviso that the oligonucleotide tags of the repertoire have a length in the range of from 12 to 60 nucleotides or base pairs; and wherein there are at least a hundred oligonucleotide tags in the repertoire.

2. A repertoire of oligonucleotide tags having a length in the range between 12 and 30 nucleotides or base pairs, the oligonucleotide tags of the repertoire being selected from the same minimally cross-hybridizing set and the oligonucleotide tags of the repertoire differing from one another by at least six nucleotides or base pairs.

3. The repertoire of claim 2 having a complexity of at least one hundred.

4. The repertoire of claim 3 having a complexity of at least one thousand.

5. A set of minimally cross-hybridizing oligonucleotides having a selected length of from 12 to 60 nucleotide bases, comprising:

a plurality of oligonucleotides, each member having:

(i) the same length as the other members of the set;
(ii) at least two base differences in oligonucleotide sequence when compared with all other members of the set;
(iii) an inability to hybridize, under stringent conditions, with any other member of the set; and
(iv) a sequence that makes substantially the same contribution to duplex stability as every other member of the set.

6. The set of claim 5, whose members all have a given length between 18 and 40 bases.

7. The set of claim 6, whose members all have a given length between 25 and 40 bases.

8. The set of claim 5, whose members are each composed of a plurality of words, each of which makes approximately the same contribution to duplex thermal stability as all other words forming the members of the set.

9. The set of claim 8, wherein each word is formed of, at most, three different bases.

10. The set of claim 8, wherein each word is a tetranucleotide.

11. The set of claim 5, wherein the oligonucleotide members are covalently attached to a solid phase support.

12. The set of claim 11, wherein each differed oligonucleotide member is attached to a selected region of a planar solid phase support, to form an array of oligonucleotides in which each array region carries a different, selected oligonucleotide member.

13. The set of claim 5, wherein each different oligonucleotide member is attached to an individual microparticle, forming a set of microparticles, each carrying a different oligonucleotide member.

* * * * *

SEQUENCE LISTING (1) GENERAL INFORMATION:

(iii) NUMBER OF SEQUENCES:  27

(2) INFORMATION FOR SEQ ID NO: 1:

(i) SEQUENCE CHARACTERISTICS:
      (A) LENGTH: 66 nucleotides
      (B) TYPE: nucleic acid
      (C) STRANDEDNESS:  single
      (D) TOPOLOGY:  linear (xi) SEQUENCE DESCRIPTION: SEQ ID NO: 1:

CTAGTCGACC ANNNNNNNNN NNNNNNNNNN NNNNNNNNNN NNNNNNNTTT     50

TTTTTTTTTT TTTTTT     66

(2) INFORMATION FOR SEQ ID NO: 2:

(i) SEQUENCE CHARACTERISTICS:
      (A) LENGTH: 39 nucleotides
      (B) TYPE: nucleic acid
      (C) STRANDEDNESS:  single
      (D) TOPOLOGY:  linear (xi) SEQUENCE DESCRIPTION: SEQ ID NO: 2:

NNNNNNNNNN NNNNNNNNNN NNNNNNNNNN NNNNNNTGG                    39

(2) INFORMATION FOR SEQ ID NO: 3:

(i) SEQUENCE CHARACTERISTICS:
        (A) LENGTH: 11 nucleotides
        (B) TYPE: nucleic acid
        (C) STRANDEDNESS: single
        (D) TOPOLOGY: linear (xi) SEQUENCE DESCRIPTION: SEQ ID NO: 3:

NRRGATCYNN N                                                   11

(2) INFORMATION FOR SEQ ID NO: 4:

(i) SEQUENCE CHARACTERISTICS:
        (A) LENGTH: 62 nucleotides
        (B) TYPE: nucleic acid
        (C) STRANDEDNESS: double
        (D) TOPOLOGY: linear (xi) SEQUENCE DESCRIPTION: SEQ ID NO: 4:

RCGACCANNN NNNNNNNNNN NNNNNNNNNN NNNNNNNNNN NNNTTTTTTT         50

TTTTTTTTTT TT                                                  62

(2) INFORMATION FOR SEQ ID NO: 5:

(i) SEQUENCE CHARACTERISTICS:
        (A) LENGTH: 38 nucleotides
        (B) TYPE: nucleic acid
        (C) STRANDEDNESS: single
        (D) TOPOLOGY: linear (xi) SEQUENCE DESCRIPTION: SEQ ID NO: 5:

GAGGATGCCT TTATGGATCC ACTCGAGATC CCAATCCA                      38

(2) INFORMATION FOR SEQ ID NO: 6:

(i) SEQUENCE CHARACTERISTICS:
        (A) LENGTH: 20 nucleotides
        (B) TYPE: nucleic acid
        (C) STRANDEDNESS: double
        (D) TOPOLOGY: linear (xi) SEQUENCE DESCRIPTION: SEQ ID NO: 6:

NNNNNNNNNN NNNNNNNNNN                                          20

(2) INFORMATION FOR SEQ ID NO: 7:

(i) SEQUENCE CHARACTERISTICS:
        (A) LENGTH: 24 nucleotides
        (B) TYPE: nucleic acid
        (C) STRANDEDNESS: double
        (D) TOPOLOGY: linear (xi) SEQUENCE DESCRIPTION: SEQ ID NO: 7:

GATCNNACTA GTNNNNNNNN NNNN                                     24

(2) INFORMATION FOR SEQ ID NO: 8:

(i) SEQUENCE CHARACTERISTICS:
        (A) LENGTH: 20 nucleotides
        (B) TYPE: nucleic acid
        (C) STRANDEDNESS: single (D) TOPOLOGY: linear (xi) SEQUENCE DESCRIPTION: SEQ ID NO: 8:

NNNNNNNNNN NNACTAGTNN                                          20

(2) INFORMATION FOR SEQ ID NO: 9:

(i) SEQUENCE CHARACTERISTICS:
        (A) LENGTH: 68 nucleotides
        (B) TYPE: nucleic acid
        (C) STRANDEDNESS: single
        (D) TOPOLOGY: linear (xi) SEQUENCE DESCRIPTION: SEQ ID NO: 9:

CTAGTCGACC ANNNNNNNNN NNNNNNNNNN NNNNNNNNNN NNNNNNNGGT         50

TTTTTTTTTT TTTTTTTT                                            68

(2) INFORMATION FOR SEQ ID NO: 10:

(i) SEQUENCE CHARACTERISTICS:
        (A) LENGTH: 11 nucleotides
        (B) TYPE: nucleic acid
        (C) STRANDEDNESS: double
        (D) TOPOLOGY: linear (xi) SEQUENCE DESCRIPTION: SEQ ID NO: 10:

ACCAGCTGAT C                                                   11

(2) INFORMATION FOR SEQ ID NO: 11:

(i) SEQUENCE CHARACTERISTICS:
        (A) LENGTH: 43 nucleotides
        (B) TYPE: nucleic acid
        (C) STRANDEDNESS: double
        (D) TOPOLOGY: linear (xi) SEQUENCE DESCRIPTION: SEQ ID NO: 11:

TCGACCGATT TGATTAGATT TGGTAAAGTA ATGTAAAGGA TTA                 43

(2) INFORMATION FOR SEQ ID NO: 12:

(i) SEQUENCE CHARACTERISTICS:
        (A) LENGTH: 43 nucleotides
        (B) TYPE: nucleic acid
        (C) STRANDEDNESS: double
        (D) TOPOLOGY: linear (xi) SEQUENCE DESCRIPTION: SEQ ID NO: 12:

TCGACCAGTA ATGTAAAGGA TTTGATAGTA TTTGTGATGA TTA                 43

(2) INFORMATION FOR SEQ ID NO: 13:

(i) SEQUENCE CHARACTERISTICS:
        (A) LENGTH: 43 nucleotides
        (B) TYPE: nucleic acid
        (C) STRANDEDNESS: double
        (D) TOPOLOGY: linear (xi) SEQUENCE DESCRIPTION: SEQ ID NO: 13:

TCGACCTAGA TGATGATTGA TTGTAAAAAG AAAGTTTGTT TGA                 43

(2) INFORMATION FOR SEQ ID NO: 14:

(i) SEQUENCE CHARACTERISTICS:
        (A) LENGTH: 42 nucleotides
        (B) TYPE: nucleic acid

```
        (C) STRANDEDNESS:  double
        (D) TOPOLOGY:  linear (xi) SEQUENCE DESCRIPTION: SEQ ID NO: 14:

GGGCCNNNNN NNNNNNNNNN NNNNNNNNNN NNNNNNNNNN NA                              42

(2) INFORMATION FOR SEQ ID NO: 15:

(i) SEQUENCE CHARACTERISTICS:
        (A) LENGTH: 26 nucleotides
        (B) TYPE: nucleic acid
        (C) STRANDEDNESS:  double
        (D) TOPOLOGY:  linear (xi) SEQUENCE DESCRIPTION: SEQ ID NO: 15:

AATTCGGATG ATGCATGCAT CGACCC                                                26

(2) INFORMATION FOR SEQ ID NO: 16:

(i) SEQUENCE CHARACTERISTICS:
        (A) LENGTH: 10 nucleotides
        (B) TYPE: nucleic acid
        (C) STRANDEDNESS:  double
        (D) TOPOLOGY:  linear (xi) SEQUENCE DESCRIPTION: SEQ ID NO: 16:

ATCGGATGAC                                                                  10

(2) INFORMATION FOR SEQ ID NO: 17:

(i) SEQUENCE CHARACTERISTICS:
        (A) LENGTH: 10 nucleotides
        (B) TYPE: nucleic acid
        (C) STRANDEDNESS:  double
        (D) TOPOLOGY:  linear (xi) SEQUENCE DESCRIPTION: SEQ ID NO: 17:

ATCCAATGAC                                                                  10

(2) INFORMATION FOR SEQ ID NO: 18:

(i) SEQUENCE CHARACTERISTICS:
        (A) LENGTH: 20 nucleotides
        (B) TYPE: nucleic acid
        (C) STRANDEDNESS:  double
        (D) TOPOLOGY:  linear (xi) SEQUENCE DESCRIPTION: SEQ ID NO: 18:

NNNAGTTGAT GTCATCCGAT                                                       20

(2) INFORMATION FOR SEQ ID NO: 19:

(i) SEQUENCE CHARACTERISTICS:
        (A) LENGTH: 20 nucleotides
        (B) TYPE: nucleic acid
        (C) STRANDEDNESS:  double
        (D) TOPOLOGY:  linear (xi) SEQUENCE DESCRIPTION: SEQ ID NO: 19:

NNNCGTTGAT GTCATCCGAT                                                       20

(2) INFORMATION FOR SEQ ID NO: 20:

(i) SEQUENCE CHARACTERISTICS:
        (A) LENGTH: 20 nucleotides
        (B) TYPE: nucleic acid
        (C) STRANDEDNESS:  double
```

(D) TOPOLOGY:  linear (xi) SEQUENCE DESCRIPTION: SEQ ID NO: 20:

NNNGGTTGAT GTCATCCGAT                                                           20

(2) INFORMATION FOR SEQ ID NO: 21:

(i) SEQUENCE CHARACTERISTICS:
            (A) LENGTH: 20 nucleotides
            (B) TYPE: nucleic acid
            (C) STRANDEDNESS:  double
            (D) TOPOLOGY:  linear (xi) SEQUENCE DESCRIPTION: SEQ ID NO: 21:

NNNTGTTGAT GTCATCCGAT                                                           20

(2) INFORMATION FOR SEQ ID NO: 22:

(i) SEQUENCE CHARACTERISTICS:
            (A) LENGTH: 44 nucleotides
            (B) TYPE: nucleic acid
            (C) STRANDEDNESS:  single
            (D) TOPOLOGY:  linear (xi) SEQUENCE DESCRIPTION: SEQ ID NO: 22:

CCCCNNNNNN NNNNNNNNNN NNNNNNNNNN NNNNNNNNNN CGGT                                44

(2) INFORMATION FOR SEQ ID NO: 23:

(i) SEQUENCE CHARACTERISTICS:
            (A) LENGTH: 20 nucleotides
            (B) TYPE: nucleic acid
            (C) STRANDEDNESS:  double
            (D) TOPOLOGY:  linear (xi) SEQUENCE DESCRIPTION: SEQ ID NO: 23:

AGTGGCTGGG CATCGGACCG                                                           20

(2) INFORMATION FOR SEQ ID NO: 24:

(i) SEQUENCE CHARACTERISTICS:
            (A) LENGTH: 20 nucleotides
            (B) TYPE: nucleic acid
            (C) STRANDEDNESS:  double
            (D) TOPOLOGY:  linear (xi) SEQUENCE DESCRIPTION: SEQ ID NO: 24:

GGGGCCCAGT CAGCGTCGAT                                                           20

(2) INFORMATION FOR SEQ ID NO: 25:

(i) SEQUENCE CHARACTERISTICS:
            (A) LENGTH: 20 nucleotides
            (B) TYPE: nucleic acid
            (C) STRANDEDNESS:  single
            (D) TOPOLOGY:  linear (xi) SEQUENCE DESCRIPTION: SEQ ID NO: 25:

AGTGGCTGGG CATCGGACCG                                                           20

(2) INFORMATION FOR SEQ ID NO: 26:

(i) SEQUENCE CHARACTERISTICS:
            (A) LENGTH: 20 nucleotides
            (B) TYPE: nucleic acid
            (C) STRANDEDNESS:  single
            (D) TOPOLOGY:  linear (xi) SEQUENCE DESCRIPTION: SEQ ID NO: 26:

ATCGACGCTG ACTGGGCCCC 20

(2) INFORMATION FOR SEQ ID NO: 27:

(i) SEQUENCE CHARACTERISTICS:
        (A) LENGTH: 62 nucleotides
        (B) TYPE: nucleic acid
        (C) STRANDEDNESS: double
        (D) TOPOLOGY: linear (xi) SEQUENCE DESCRIPTION: SEQ ID NO: 27:

AAAAGGAGGA GGCCTTGATA GAGAGGACCT GTTTAAACGG ATCCTCTTCC 50

TCTTCCTCTT CC 62